(12) United States Patent
Bae et al.

(10) Patent No.: US 10,478,445 B2
(45) Date of Patent: Nov. 19, 2019

(54) BORONIC ACID DERIVATIVES OF RESVERATROL FOR ACTIVATING DEACETYLASE ENZYMES

(71) Applicant: Georgetown University, Washington, DC (US)

(72) Inventors: Insoo Bae, Springfield, VA (US); Yong Weon Yi, Arlington, VA (US); Hyo Jin Kang, Fairfax, VA (US); Hee Jeong Kim, Springfield, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/902,783

(22) PCT Filed: Jul. 3, 2014

(86) PCT No.: PCT/US2014/045437
§ 371 (c)(1),
(2) Date: Jan. 4, 2016

(87) PCT Pub. No.: WO2015/003146
PCT Pub. Date: Jan. 8, 2015

(65) Prior Publication Data
US 2016/0166592 A1 Jun. 16, 2016

Related U.S. Application Data

(60) Provisional application No. 61/842,629, filed on Jul. 3, 2013.

(51) Int. Cl.
*A61K 31/69* (2006.01)
(52) U.S. Cl.
CPC .................................. *A61K 31/69* (2013.01)
(58) Field of Classification Search
None
See application file for complete search history.

(56) References Cited

U.S. PATENT DOCUMENTS

| | | |
|---|---|---|
| 3,046,121 A | 7/1962 | Schmidt |
| 3,965,703 A | 6/1976 | Barnhardt |
| 4,499,082 A | 2/1985 | Shenvi |
| 5,169,841 A | 12/1992 | Kleeman |
| 5,187,157 A | 2/1993 | Kettner |
| 5,242,904 A | 9/1993 | Kettner |
| 5,250,720 A | 10/1993 | Kettner |
| 5,677,328 A | 10/1997 | Takaki |
| 5,780,454 A | 7/1998 | Adams |
| 6,037,362 A | 3/2000 | Miyoshi |
| 6,066,730 A | 5/2000 | Adams |
| 6,083,903 A | 7/2000 | Adams |
| 6,297,217 B1 | 10/2001 | Adams |
| 6,572,882 B1 | 6/2003 | Vercauteren |

FOREIGN PATENT DOCUMENTS

| | | |
|---|---|---|
| EP | 0773020 | 4/2005 |
| WO | 9904747 | 2/1999 |
| WO | 9958119 | 11/1999 |
| WO | 9959561 | 11/1999 |
| WO | 2011020107 | 2/2011 |
| WO | 2011022502 | 2/2011 |
| WO | 2012027482 | 3/2012 |

OTHER PUBLICATIONS

Athar, et al., "Resveratrol: a review of preclinical studies for human cancer prevention", Toxicol Appl Pharmacol, 224(3):274-83 (2007).
Baur and Sinclair, "Therapeutic potential of resveratrol: the in vivo evidence" Nat Rev Drug Discov, 5;493-506 (2006).
Boocock, et al., "Phase I dose escalation pharmacokinetic study in healthy volunteers of resveratrol, a potential cancer chemopreventive agent", Cancer Epidemiol Biomarkers Prev, 16:1246-52 (2007).
Ciechanover, "The ubiquitin-proteasome proteolytic pathway", Cell, 79:13-21 (1994).
Dorsey et al., "Discovery of a potent, selective, and orally active proteasome inhibitor for the treatment of cancer", J. Med Chem, 51:1068-72 (2008).
Hain, et al "Expression of a stilbene synthase gene in Nicotiana tabacum results in synthesis of the phytoalexin resveratrol", Plant Mol Biol, 15:325-35 (1990).
Heynekamp, et al., "Substituted trans-stilbenes, including analogues of the natural product resveratrol, inhibit the human tumor necrosis factor alpha-induced activation of transcription factor nuclear factor kappaB", J Med Chem 49:7182-9 (2006).
Howitz, et al., "Small molecule activators of sirtuins extend *Saccharomyces cerevisiae* lifespan", Nature, 425:191-6 (2003).
Jang, et al., "Cancer chemopreventive activity of resveratrol, a natural product derived from grapes", Science, 275:218-20 (1997).
Kong, et al., "A boronic acid chalcone analog of combretastatin A-4 as a potent anti-proliferation agent", Bioorganic Med Chem., 18(2):971-7 (2010).
Kong, et al., "Structure-based discovery of a boronic acid bloisostere of combretastatin A-4", Chem Biol, 12:1007-14 (2005).
Kundu and Surh, "Cancer chemopreventive and therapeutic potential of resveratrol: mechanistic perspectives", Cancer Lett, 269:243-61 (2008).
Kupperman, et al., "Evaluation of the proteasome inhibitor MLN9708 in preclinical models of human cancer", Cancer Res, 70:1970-80 (2010).
Lakshimanrasimhan, et al., "Sirt1 activation by resveratrol is substrate sequence-selective", Aging, 5:151-4 (2013).
Leifert and Abeywardena, "Cardioprotective actions of grape polyphenols", Nutr Res, 28:729-37 (2008).

(Continued)

*Primary Examiner* — Brian J Davis
(74) *Attorney, Agent, or Firm* — Pabst Patent Group LLP

(57) ABSTRACT

Disclosed herein are compounds, compositions and methods for the treatment of a disease or disorder related to activation of deacetylase enzymes. The compounds and methods are related to boronic acid derivatives of resveratrol. In some forms, the compound, compositions and methods relate to treatment of prostate cancer, colon cancer, or breast cancer, a cardiovascular disease, inflammation, obesity, diabetes, or a neurodegenerative disease.

21 Claims, 7 Drawing Sheets

(56) References Cited

OTHER PUBLICATIONS

Lion, et al., "Synthesis, antitumor evaluation, and apoptosis-inducing activity of hydroxylated (E)-stilbenes", J Med Chem, 48:1292-5 (2005).

Ma, et al., "Resveratrol analog trans 3,4,5,4-tetramethoxystilbene (DMU-212) mediates anti-tumor effects via mechanism different from that of resveratrol", Cancer Chemother Pharmacol, 63:27-35 (2008).

Martinez and Oreno, "Effect of resveratrol, a natural polyphenolic compound, on reactive oxygen species and prostaglandin production", Biochem Pharmacol 59:865-70 (2000).

Milne, et al., "Small molecule activators of SIRT1 as therapeutics for the treatment of type 2 diabetes", Nature, 450:712-6 (2007).

Minor, et al., "SRT1720 improves survival and healthspan of obese mice", Sci Rep, 1:70 (2011).

Minutolo, et al., "Synthesis of a resveratrol analogue with high ceramide-mediated proapoptotic activity on human breast cancer cells", J Med Chem, 48:6783-6 (2005).

Nayagam, et al, "SIRT1 modulating compounds from high-throughput screening as anti-inflammatory and insulin-sensitizing agents", J Biomol Screen, 11:859-67 (2006).

Niles, et al., "Resveratrol is rapidly metabolized in athymic (nu/nu) mice and does not inhibit human melanoma xenograft tumor growth", J Nutr., 136:2542-6 (2006).

Orsini, et al., "Isolation, synthesis, and antiplatelet aggregation activity of resveratrol 3-O-beta-D-glucopyranoside and related compounds", J Nat Prod, 60:1082-7 (1997).

Pace-Asciak, et al., "Wines and grape juices as modulators of platelet aggregation in healthy human subjects", Clin Chim Acta, 246:163-82 (1996).

Pan, et al., "3,5,3',4',5'—pentamethoxystilbene (MR-5), a synthetically methoxylated analogue of resveratrol, inhibits growth and induces G1 cell cycle arrest of human breast carcinoma MCF-7 cells", J. Agric. Food Chem. 58:226-34 (2010).

Roberti, et al., "Synthesis and biological evaluation of resveratrol and analogues as apoptosis-inducing agents", J Med Chem, 46:3546-54 (2003).

Signorelli and Ghidoni, "Resveratrol as an anticancer nutrient: molecular basis, open questions and promises", J Nutr Biochem, 16:449-66 (2005).

Tondi, et al., "Structural study of phenyl boronic acid derivatives as AmpC beta-lactamase inhibitors", Bioorg Med Chem Lett, 20(11):3416-9 (2010).

Walle, et al., "High absorption but very low bioavailability of oral resveratrol in humans", Drug Metab Dispos, 32:1377-82 (2004).

Wenzel, et al, "Bioactivity and metabolism of trans-resveratrol orally administered to Wistar rats", Mol Nutr Food Res, 49:482-94 (2005).

Werz, et al., "Nonredox 5-lipoxygenase inhibitors require glutathione peroxidase for efficient inhibition of 5-lipoxygenase activity", Mol Pharmacol 54:445-51 (1998).

Yl, et al., "Targeting mutant p53 by a SIRT1 activator YK-3-237 inhibits the proliferation of triple-negative breast cancer cells", Oncotarget, 4(7):984-94 (2013).

International Search Report for PCT/US2014/045437 dated Jan. 13, 2014.

(A)

(B)

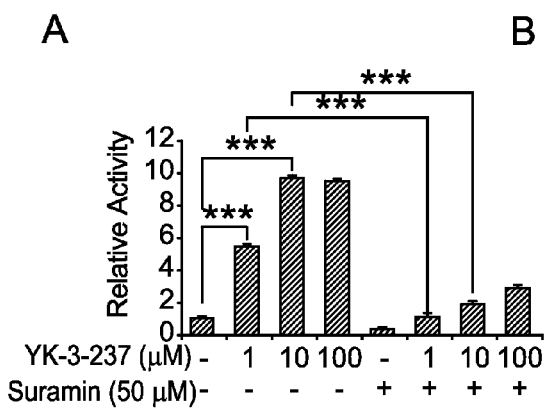
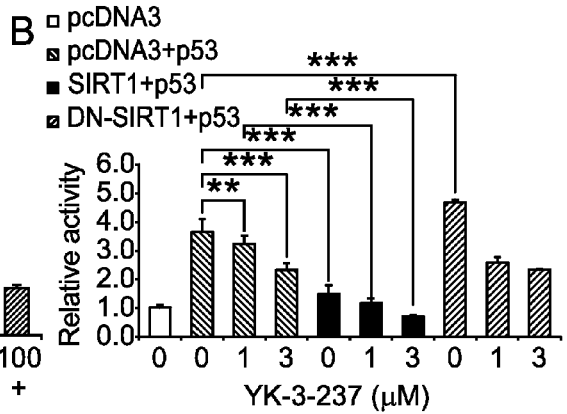
FIG. 4A    FIG. 4B
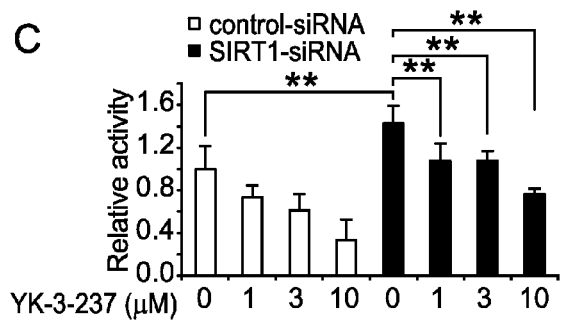
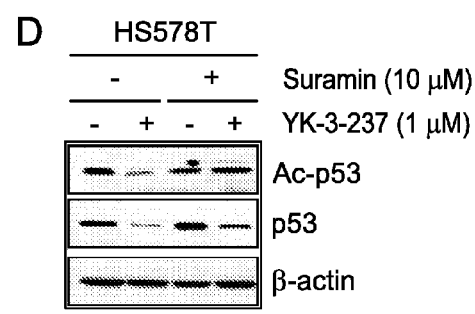
FIG. 4C    FIG. 4D
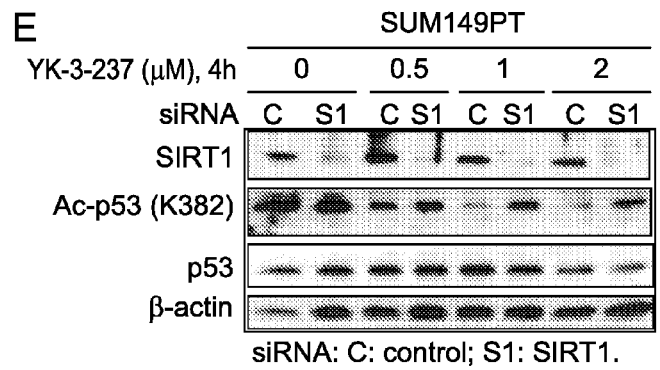
FIG. 4E

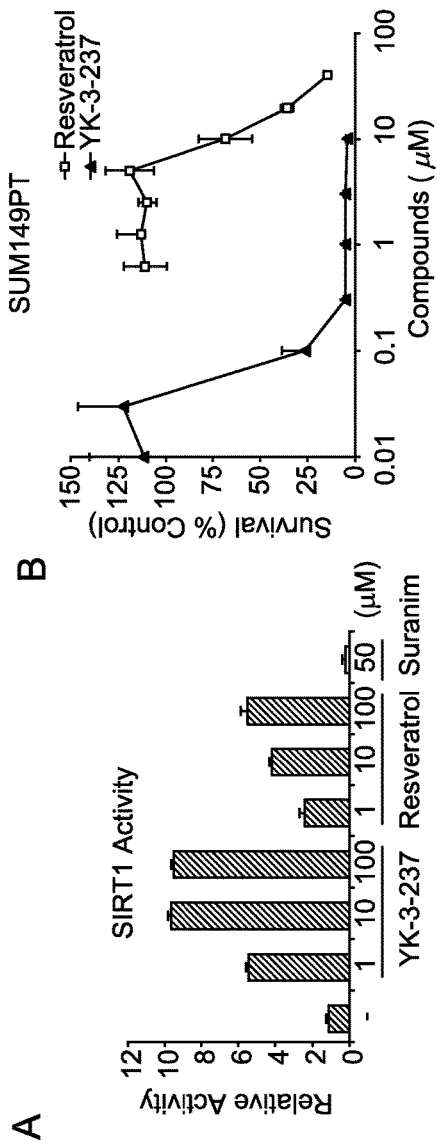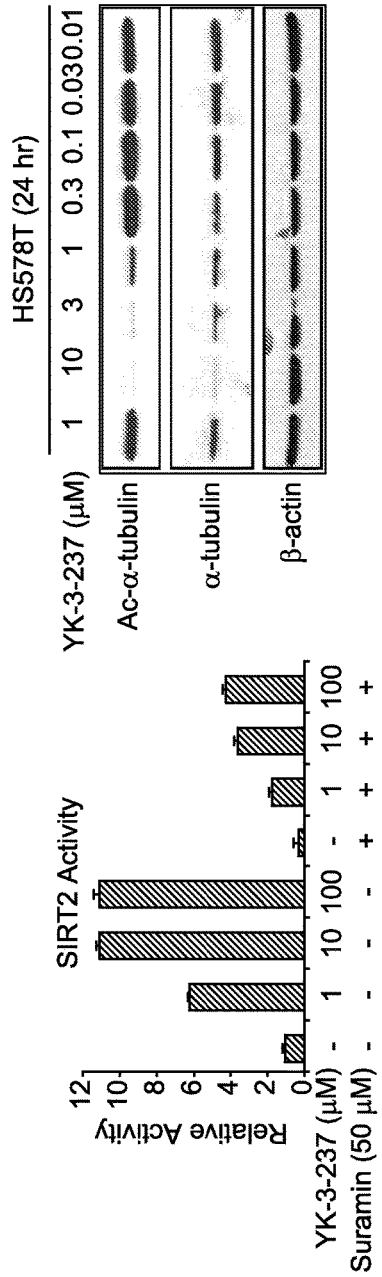
FIG. 5A
FIG. 5B
FIG. 5C
FIG. 5D

BORONIC ACID DERIVATIVES OF RESVERATROL FOR ACTIVATING DEACETYLASE ENZYMES

CROSS-REFERENCE TO RELATED APPLICATIONS

This application is a 371 application of International Application No. PCT/US2014/045437, filed Jul. 3, 2014, which claims priority to U.S. Provisional Application No. 61/842,629, Jul. 3, 2013.

STATEMENT REGARDING FEDERALLY SPONSORED RESEARCH

This invention was made with government support under 1R03CA152530 awarded by the National Institutes of Health (NIH). The government has certain rights in the invention.

FIELD OF THE INVENTION

The disclosed invention is generally in the field of small molecule activators of deacetylase enzymes and the treatment of disorders including cancer, cardiovascular disease, inflammation, obesity, diabetes, and neurodegenerative diseases related to the activation of deacetylase enzymes.

BACKGROUND OF THE INVENTION

Histone tails contain highly conserved lysine residues that can be acetylated on their ε-amino groups. Each acetylation event eliminates another positive charge and potentially weakens the electrostatic interactions that tether the octamer tails to the DNA phosphate backbone. Histone acetylation may affect chromatin structure by at least two different mechanisms. First, the net reduction in positive charge could lead to destabilization and consequent dissociation of nucleosomes, thus allowing access of transcription factors and RNA polymerase to the DNA. Second, histone acetylation may inhibit the stacking of nucleosomes into the solenoid structure and thus the formation of higher-order structure. In addition, several cellular proteins are also regulated by acetylation of their lysine residues. The acetylation/deacetylation of proteins regulates the function of proteins in several ways.

Two families of deacetylase enzymes have been identified: the histone deacetylases, or HDACs, and the Sir2 (silent information regulator)-like family of NAD-dependent deacetylases, or sirtuins. The HDACs and sirtuin enzymes are therapeutic targets in a variety of human diseases including cancer, diabetes, inflammatory disorders and neurodegenerative disease. For example, modulation of sirtuin activity has been shown to impact the course of several aggregate-forming neurodegenerative disorders including Alzheimer's disease, Parkinson's disease, Huntington's disease, amyotrophic lateral sclerosis and spinal and bulbar muscular atrophy. Sirtuins can influence the progression of neurodegenerative disorders by modulating transcription factor activity and directly deacetylating proteotoxic species.

Sirtuin activation through the polyphenol resveratrol can regulate metabolism and the aging processes in yeast and higher organisms, and SIRT1 activation can alleviate metabolic diseases in mice (Lakshimanrasimhan, Aging, 5:151-154, 2013). Resveratrol (RSV) is a natural compound found in the skin of red grapes and other food products that seems to have a wide spectrum of biological activities which includes phytoalexin to protect plants against the fungal infection (Plant Mol Biol, 15:325-335, 1990), as a cardioprotective agent (Nutr Res, 28:729-737, 2008), partially preventing platelet aggregation (Clin Chim Acta, 246:163-182, 1996; J Nat Prod, 60:1082-1087, 1997), and inhibiting 5-lipoxygenase activity and prostaglandin synthesis (Mol Pharmacol 54:445-451, 1998; Biochem Pharmacol 59:865-870, 2000). Use of resveratrol in the pharmaceutical and cosmetic fields is described in, for example, WO9959561, WO9958119, EP0773020, FR2766176, and WO9904747.

There is an interest in resveratrol as a chemo-preventive agent in cancer therapy based on its striking inhibitory effects on cellular events associated with cancer initiation, promotion and propagation (Science, 275:218, 1997; J Nutr Biochem, 16:449, 2005; Cancer Lett, 269:243, 2008). Previous studies on in vitro anti-cancer effects of resveratrol showed that it interacts with multiple molecular targets and has positive effects on different cancer cells including breast, skin, gastric, colon, prostate, leukemia (Nat Rev Drug Discov, 5:493, 2006). However, the study of pharmacokinetics of resveratrol in humans concluded that even high doses of resveratrol might be insufficient to achieve resveratrol concentrations required for the systemic prevention of cancer (Toxicol Appl Pharmacol, 224:274, 2007) because of its lower bioavailability and its quick metabolization as sulfo and glucuro conjugates (Cancer Epidemiol. Biomarkers Prev, 16:1246, 2007, J Nutr, 136:2542, 2006 Drug Metab Dispos, 32:1377, 2004 Mol Nutr Food Res, 49:482, 2005). Other studies have focused on the design and synthesis of novel resveratrol analogs with more potent antitumor activity and a better pharmacokinetic profile (J Med Chem, 46:3546, 2003 J Med Chem, 48:1292, 2005, J Med Chem, 48:6783, 2005 Cancer Chemother Pharmacol, 63:27, 2008, J Med Chem 49, 7182, 2006 J. Agric. Food Chem. 58, 226, 2010).

There are reports on a boronic acid biostere of combrestatin A-4 and a chalcone analog of combrestatin A-4 as potent anti-cancer agents (Chem Biol, 12:1007, 2005, Bioorg. Med Chem, 18, 971, 2010). In addition, boronic acid and ester compounds have been reported to display a variety of pharmaceutically useful biological activities as proteosome inhibitors and several important functions including reduction in the rate of muscle protein degradation, reduction in the activity of NF-kB in a cell, inhibition in the cyclin degradation in a cell, inhibition in the growth of cancer cells, and inhibition of antigen presentation in a cell (Cell, 79:13-21, 1991; Cancer Res, 70:1970-80, 2010, Bioorg Med Chem Lett, 10:3416-9, 2010 J. Med Chem, 51:1068-1072, 2008, U.S. Pat. Nos. 4,499,082, 5,187,157, 5,242,904, 5,250,720, 5,169,841, 5,780,454, 6,066,730, 6,083,903, 6,297,217).

It is an object of this invention to provide compounds, compositions and methods to activate deacetylase enzymes. It is also an object of the present invention to provide compounds, compositions and methods for the treatment of cancer, cardiovascular disease, inflammation, obesity, diabetes, or a neurodegenerative disease related to the activation of deacetylase enzymes.

BRIEF SUMMARY OF THE INVENTION

Disclosed herein are compounds, compositions and methods for the treatment of a disease or disorder related to activation of deacetylase enzymes. The compounds and methods are related to boronic acid derivatives of resveratrol.

In some forms, the compounds, compositions and methods relate to the formula A-L-C, or pharmaceutically acceptable salt, prodrug, clathrate, tautomer or solvate thereof, wherein:

A is substituted or unsubstituted cycloalkyl, aryl, heteroaryl, heterocyclyl;

L is present or absent, and, if present, L is a linker; and

C is substituted or unsubstituted cycloalkyl, aryl, heteroaryl, heterocyclyl, wherein at least one position in the compound is substituted with —B(OH)$_2$, and at least one position in the compound is substituted with alkoxy, alkoxydialkylamino or hydroxyl.

In some forms, the compound, compositions and methods relate to treatment of prostate cancer, colon cancer, leukemia, non-small cell lung cancer, melanoma, CNS cancer, ovarian cancer, renal cancer, or breast cancer. In some forms, the cancer can be triple negative breast cancer (TNBC). In some forms, the compound, compositions and methods relate to treatment of cancers the cells of which express mutant p53. In some forms, the compound, compositions and methods relate to treatment of cancers the cells of which under-express SIRT1. In some forms, the compound, compositions and methods relate to treatment to reduce the risk of age-related cancers. In some forms, the compound, compositions and methods relate to treatment to reduce the risk of age-related cancers in subjects the cells of which express mutant p53.

In some forms, the compound, compositions and methods relate to treatment of a cardiovascular disease, inflammation, obesity, diabetes, or a neurodegenerative disease.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows the structure of YK-3-237. FIG. 1B is a bar graph showing the relative sensitivities of breast cancer cell lines to YK-3-237. Breast cancer cells were treated with increasing amount of YK-3-237 for approximately 72 hr and the viable cells were measured by MTT assay. FIG. 1C is a western blot analysis of breast cancer cell lines. Cell lysates from each cell line were analysed by indicated antibodies. FIG. 1D shows the effect of YK-3-237 on the level of mtp53. Cells were treated with 1 μM of YK-3-237 for 24 hr and western blot analysis was performed with indicated antibodies. FIG. 1E shows YK-3-237 reduces acetyl-mtp53. Cells were treated with increasing concentrations of YK-3-237 for 24 hr and cell lysates were subjected to western blot analysis with indicated antibodies.

FIG. 3A is a western blot showing cells treated with different concentrations of compound YK-3-237 for 24 hr. FIG. 3B is a western blot showing cells treated with 1 μM of compound YK-3-237 for indicated time.

FIG. 4A-4E show the effect of compound YK-3-237 on the activity of SIRT1. FIG. 4A is a bar graph showing the effect of compound YK-3-237 on the enzyme activity of purified human SIRT1 enzyme in vitro. FIG. 4B is a bar graph showing the effect of compound YK-3-237 on the SIRT1-mediated repression of wild type p53 (WTp53) transcriptional activity. MCF7 cells were transfected with indicated plasmid DNAs and further treated with YK-3-237 for 24 hr. FIG. 4C is a bar graph showing SIRT1-KD reverses compound YK-3-237-mediated repression of WTp53 transcriptional activity. MCF7 cells were transfected with siRNA and p53-Luc and further treated with YK-3-237 for 24 hr. FIG. 4D is a western blot showing that suramin reduces compound YK-3-237-mediated deacetylation of mtp53. HS578T cells, pretreated with suramin for 1 hr, were further treated with compound YK-3-237 for 23 hr. FIG. 4E is a western blot showing the effect of compound YK-3-237 on the SIRT1-mediated deacetylation of mtp53. SUM149PT cells were transfected with either control siRNA (C-siRNA) or SIRT1-siRNA (S1-siRNA) for 3 days, re-seeded and further treated with YK-3-237 for 4 hr. Western blot analysis was conducted with indicated antibodies. β-Actin was used as a loading control.

FIG. 5A-5D shows the effect of compound YK-3-237 and resveratrol on enzyme activity. FIG. 5A shows the effect of compound YK-3-237 and resveratrol on the enzyme activity of purified human SIRT1 enzyme in vitro. For compound YK-3-237, the same data from FIG. 4A were used. FIG. 5B shows the effect of compound YK-3-237 and resveratrol on the survival of SUM149PT cells. SUM149PT cells (250 cells/well) were treated with increasing amount of YK-3-237 or resveratrol for 3 days. The cells were then replenished with fresh media without the compound and further cultivated for additional 4 days. The surviving colonies were stained by MTT assay. Data are presented as mean±SD from the experiment performed in triplicate. FIG. 5C shows the effect of YK-3-237 on the enzyme activity of purified human SIRT2 enzyme in vitro. Data are presented as mean±SD. FIG. 5D shows the effect of compound YK-3-237 on the acetylation of α-tubulin. HS578T cells were treated with increasing amount of YK-3-237 for 24 hr and the cell lysates were subjected to western blot analysis with indicated antibody. β-Actin was used as a loading control.

FIG. 6A shows the effect of mtp53 knockdown on the expression of WTp53-target genes. Cells were transfected with either control-siRNA (C-siRNA) or p53-siRNA and subjected to quantitative RT-PCR. Knockdown of mtp53 was assessed by western blot analysis. FIG. 6B shows a quantitative RT-PCR analysis of WTp53-target genes in cells treated with compound YK-3-237. Cells were treated with compound YK-3-237 for 24 hr and quantitative RT-PCR was performed as in A.

In FIG. 7A, β-Actin was used as a loading control.

DETAILED DESCRIPTION OF THE INVENTION

Figure 1A:
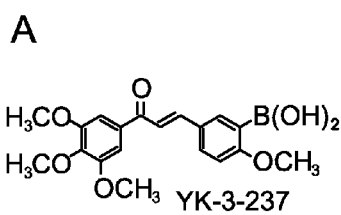
FIG. 1A-1E shows the reduction in proliferation and acetylation of mutant p53 (mtp53) in breast cancer cell lines by compound YK-3-237.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an activator of inhibitor is disclosed and discussed and a number of modifications that can be made to a number of R groups are discussed, each and every combination and permutation of activator or inhibitor and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The term binding affinity as used herein can be defined as two molecules interacting with a kd of at least 10-3, 10-4, 10-5, 10-6, 10-7, 10-8, or 10-9 M or tighter binding.

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

The term complex as used herein refers to the association of a compound with another composition for which the compound has a binding affinity.

"Coapplication" is defined as the application of one or more substances simultaneously, such as in the same formulation or consecutively, within a time frame such that each substance is active during a point when the other substance or substances are active.

Throughout the description and claims of this specification, the word "comprise" and variations of the word, such as "comprising" and "comprises," means "including but not limited to," and is not intended to exclude, for example, other additives, components, integers or steps.

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

"Optional" or "optionally" means that the subsequently described event or circumstance may or may not occur, and that the description includes instances where said event or circumstance occurs and instances where it does not.

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

By "risk" or "increased risk" is meant that the chance of the event or condition referenced is greater than a normal, average, or other comparison risk. For example, in the context of cancer, most individuals have some risk of cancer and the average or normal risk of cancer is not zero. In this context, an increased risk would mean that the individual has a greater chance of developing cancer than the normal or average individual.

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

As used herein, the terms "linked", "operably linked" and "operably bound" and variants thereof mean, for purposes of the specification and claims, to refer to fusion, bond, adherence or association of sufficient stability to withstand conditions encountered in single molecule applications and/or the methods and systems disclosed herein, between a combination of different molecules such as, but not limited to: between a detectable label and nucleotide, between a detectable label and a linker, between a nucleotide and a linker, between a protein and a functionalized nanocrystal; between a linker and a protein; and the like. For example, in a labeled polymerase, the label is operably linked to the polymerase in such a way that the resultant labeled polymerase can readily participate in a polymerization reaction. See, for example, Hermanson, G., 2008, Bioconjugate Techniques, Second Edition. Such operable linkage or binding may comprise any sort of fusion, bond, adherence or association, including, but not limited to, covalent, ionic, hydrogen, hydrophilic, hydrophobic or affinity bonding, affinity bonding, van der Waals forces, mechanical bonding, etc.

The term "linker" and its variants, as used herein, include any compound or moiety that can act as a molecular bridge that operably links two different molecules.

The term "metabolite" refers to active derivatives produced upon introduction of a compound into a biological milieu, such as a patient.

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year and preferably more than 18 months. As used herein, the term "stable" references these market realities and the ability to store and transport the product at readily attainable environmental conditions such as refrigerated conditions, 2° C. to 8° C.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

In this specification and in the claims which follow, reference will be made to a number of terms which shall be defined to have the following meanings:

The term "compound 1" and "YK-3-237" are interchangeable throughout the specification.

"Optional" or "optionally" means that the subsequently described event or circumstance may or may not occur, and that the description includes instances where said event or circumstance occurs and instances where it does not.

"Overexpression" refers to expression of a gene or protein that is greater than the normal or average expression for normal or typical cells, or of cells of the same type. For example, if a breast cell exhibits higher expression of a gene or protein than the normal expression of normal breast cells, that breast cell can be said to overexpress that gene or protein. Similarly, if a cancer cell exhibits higher expression of a gene or protein than the typical expression of typical cancer cells of the same type, that cancer cell can be said to overexpress that gene or protein. As another example, if a breast cancer cell exhibits higher expression of a gene or protein than the typical expression of typical breast cancer cells, that breast cancer cell can be said to overexpress that gene or protein. As another example, if a breast cancer cell exhibits higher expression of a gene or protein than the normal expression of normal breast cells, that breast cancer cell can be said to overexpress that gene or protein. Thus, overexpression generally will be in reference to a normal or typical expression level and can differ depending on what is used for the comparison or reference expression level.

"Under-expression" refers to expression of a gene or protein that is lower than the normal or average expression for normal or typical cells, or of cells of the same type. For example, if a breast cell exhibits lower expression of a gene or protein than the normal expression of normal breast cells, that breast cell can be said to under-express that gene or protein. Similarly, if a cancer cell exhibits lower expression of a gene or protein than the typical expression of typical cancer cells of the same type, that cancer cell can be said to under-express that gene or protein. As another example, if a breast cancer cell exhibits lower expression of a gene or protein than the typical expression of typical breast cancer cells, that breast cancer cell can be said to under-express that gene or protein. As another example, if a breast cancer cell exhibits lower expression of a gene or protein than the normal expression of normal breast cells, that breast cancer cell can be said to under-express that gene or protein. Thus, under-expression generally will be in reference to a normal or typical expression level and can differ depending on what is used for the comparison or reference expression level.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "alkyl" as used herein is a branched or unbranched saturated hydrocarbon moiety. "Unbranched" or "Branched" alkyls comprise a non-cyclic, saturated, straight or branched chain hydrocarbon moiety having from 1 to 24 carbons, 1 to 12, carbons, 1 to 6 carbons, or 1 to 4 carbon atoms. Examples of such alkyl radicals include methyl, ethyl, propyl, butyl, pentyl, hexyl, heptyl, octyl, n-propyl, iso-propyl, butyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms, i.e., C1-C4 alkyl.

Moreover, the term "alkyl" as used throughout the specification and claims is intended to include both "unsubstituted alkyls" and "substituted alkyls", the later denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. It will be understood by those skilled in the art that an "alkoxy" can be a substituted of a carbonyl substituted "alkyl" forming an ester. When more than one substituent group is present then they can be the same or different. The organic substituent moieties can comprise from 1 to 12 carbon atoms, or from 1 to 6 carbon atoms, or from 1 to 4 carbon atoms. It will be understood by those skilled in the art that the moieties substituted on the "alkyl" chain can themselves be substituted, as described above, if appropriate.

The term "alkenyl" as used herein is an alkyl residue as defined above that also comprises at least one carbon-carbon double bond in the backbone of the hydrocarbon chain. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" as used herein is an alkyl residue as defined above that comprises at least one carbon-carbon triple bond in the backbone of the hydrocarbon chain. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "cycloalkyl" as used herein is a saturated hydrocarbon structure wherein the structure is closed to form at least one ring. Cycloalkyls typically comprise a cyclic radical containing 3 to 8 ring carbons, such as cyclopropyl, cyclobutyl, cyclopentyl, cyclopenyl, cyclohexyl, cycloheptyl and the like. Cycloalkyl radicals can be multicyclic and can contain a total of 3 to 18 carbons, or preferably 4 to 12 carbons, or 5 to 8 carbons. Examples of multicyclic cycloalkyls include decahydronapthyl, adamantyl, and like radicals.

Moreover, the term "cycloalkyl" as used throughout the specification and claims is intended to include both "unsubstituted cycloalkyls" and "substituted cycloalkyls", the later denotes an cycloalkyl radical analogous to the above definition that is further substituted with one, two, or more additional organic or inorganic substituent groups that can include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

The term "cycloalkenyl" as used herein is a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like.

The term "alkoxy" as used herein is an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like.

The term "mono-substituted amino" as used herein is a moiety comprising an NH radical substituted with one organic substituent group, which include but are not limited to alkyls, substituted alkyls, cycloalkyls, aryls, or arylalkyls. Examples of mono-substituted amino groups include methylamino (—NH—CH3); ethylamino (—NHCH2CH3), hydroxyethylamino (—NH—CH2CH2OH), and the like.

As used herein, the term "azide", "azido" and their variants refer to any moiety or compound comprising the monovalent group —N3 or the monovalent ion —N3.

The term "di-substituted amino" as used herein is a moiety comprising a nitrogen atom substituted with two organic radicals that can be the same or different, which can be selected from but are not limited to aryl, substituted aryl, alkyl, substituted alkyl or arylalkyl, wherein the terms have the same definitions found throughout. Some examples include dimethylamino, methylethylamino, diethylamino and the like.

The term "haloalkyl" as used herein an alkyl residue as defined above, substituted with one or more halogens, preferably fluorine, such as a trifluoromethyl, pentafluoroethyl and the like.

The term "haloalkoxy" as used herein a haloalkyl residue as defined above that is directly attached to an oxygen to form trifluoromethoxy, pentafluoroethoxy and the like.

The term "acyl" as used herein is a R—C(O)— residue having an R group containing 1 to 8 carbons. Examples include but are not limited to formyl, acetyl, propionyl, butanoyl, iso-butanoyl, pentanoyl, hexanoyl, heptanoyl, benzoyl and the like, and natural or un-natural amino acids.

The term "acyloxy" as used herein is an acyl radical as defined above directly attached to an oxygen to form an R—C(O)O— residue. Examples include but are not limited to acetyloxy, propionyloxy, butanoyloxy, iso-butanoyloxy, benzoyloxy and the like.

The term "aryl" as used herein is a ring radical containing 6 to 18 carbons, or preferably 6 to 12 carbons, comprising at least one aromatic residue therein. Examples of such aryl radicals include phenyl, naphthyl, and ischroman radicals. Moreover, the term "aryl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "aryl" can themselves be substituted, as described above, if appropriate.

The term "heteroaryl" as used herein is an aryl ring radical as defined above, wherein at least one of the ring carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can comprise from 1 to 12 carbon atoms, or from 1 to 6 carbon atoms, or from 1 to 4 carbon atoms.

The term "heterocyclyl" or "heterocyclic group" as used herein is a non-aromatic mono- or multi ring radical structure having 3 to 16 members, preferably 4 to 10 members, in which at least one ring structure include 1 to 4 heteroatoms (e.g. O, N, S, P, and the like). Heterocyclyl groups include, for example, pyrrolidine, oxolane, thiolane, imidazole, oxazole, piperidine, piperizine, morpholine, lactones, lactams, such as azetidiones, and pyrrolidiones, sultams, sultones, and the like. Moreover, the term "heterocyclyl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "heterocyclyl" can themselves be substituted, as described above, if appropriate.

The term "halo" or "halogen" refers to a fluoro, chloro, bromo or iodo group.

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

A "moiety" is part of a molecule (or compound, or analog, etc.). A "functional group" is a specific group of atoms in a molecule. A moiety can be a functional group or can include one or functional groups.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula OC(O)OR, where R can be hydrogen, an alkyl, alkenyl, alkynyl, aryl, aralkyl, cycloalkyl, halogenated alkyl, or heterocycloalkyl group described above.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

The term "aldehyde" as used herein is represented by the formula —C(O)H.

The term "carboxylic acid" as used herein is represented by the formula C(O)OH.

The term "carbonyl group" as used herein is represented by the formula C=O.

The term "ether" as used herein is represented by the formula AOA1, where A and A1 can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The term "sulfo-oxo group" as used herein is represented by the formulas $S(O)_2R$, $OS(O)_2R$, or, $-OS(O)_2OR$, where R can be hydrogen, an alkyl, alkenyl, alkynyl, aryl, aralkyl, cycloalkyl, halogenated alkyl, or heterocycloalkyl group described above.

The term "alkoxy" as used herein is an alkyl group bound through a single, terminal ether linkage; that is, an "alkoxy" group may be defined as —OR where R is alkyl as defined above. A "lower alkoxy" group is an alkoxy group containing from one to six carbon atoms.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

$R^1$, $R^2$, $R^3$, $R^4$, $R^5$, $R^6$, $R^7$, $R^8$, $R^9$ and $R^{10}$ can, independently, possess two or more of the groups listed above. For example, if $R^1$, $R^2$, $R^3$, $R^4$, $R^5$, $R^6$, $R^7$, $R^8$, $R^9$ or $R^{10}$ is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

B. Compositions and Methods

The disclosed methods involve administration of compounds and compositions. The effect desired determines the compounds and compositions to be used.

The compounds disclosed herein are boronic acid analogs of resveratrol, for example,

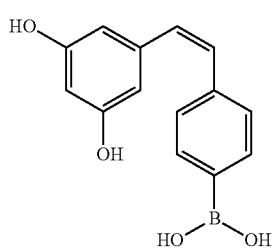

Compound 1

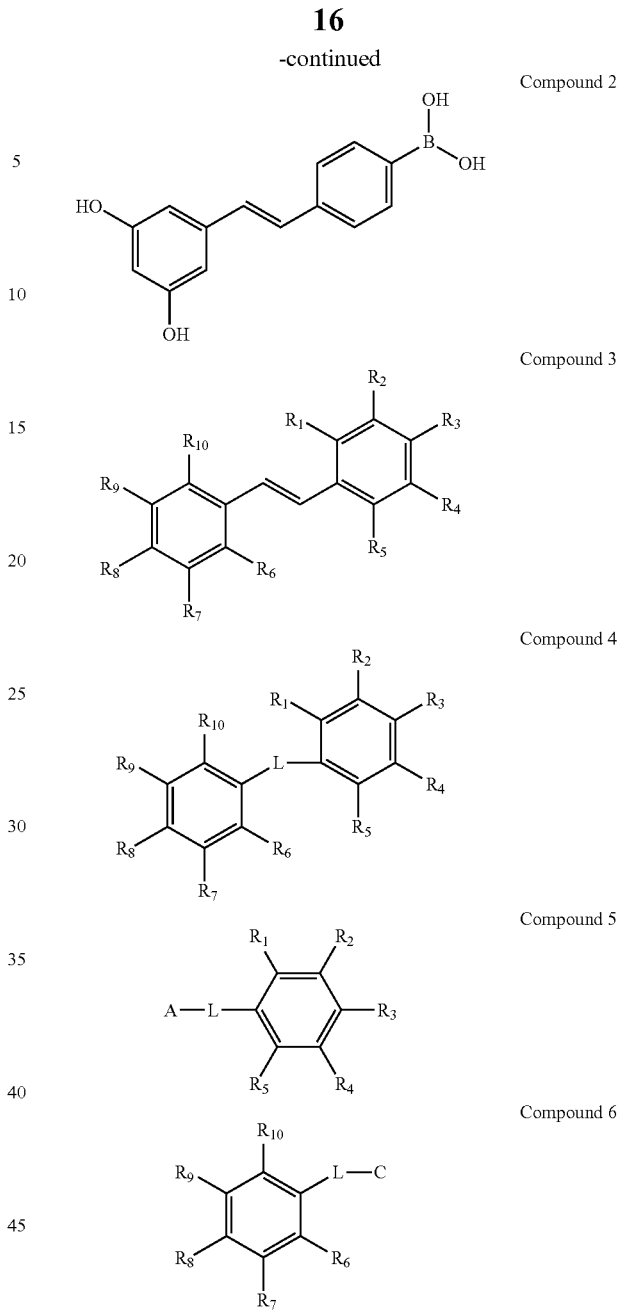

Disclosed herein are compounds of structure A-L-C, or a pharmaceutically acceptable salt, prodrug, clathrate, tautomer or solvate thereof, wherein:

A is substituted or unsubstituted cycloalkyl, aryl, heteroaryl, heterocyclyl;

L is present or absent, if present L is a linker; and

C is substituted or unsubstituted cycloalkyl, aryl, heteroaryl, heterocyclyl, wherein at least one position in the compound is substituted with —B(OH)$_2$, and at least one position is substituted with alkoxy, alkoxydialkylamino or hydroxyl.

Also disclosed herein are compositions or a pharmaceutically acceptable salt, prodrug, clathrate, tautomer or solvate thereof comprising, compounds of structure A-L-C, or a pharmaceutically acceptable salt, prodrug, clathrate, tautomer or solvate thereof, wherein:

A is substituted or unsubstituted cycloalkyl, aryl, heteroaryl, heterocyclyl;

L is present or absent, if present L is a linker; and

C is substituted or unsubstituted cycloalkyl, aryl, heteroaryl, heterocyclyl, wherein at least one position is substituted with —B(OH)$_2$, and at least one position is substituted with alkoxy, alkoxydialkylamino or hydroxyl.

Also disclosed herein are methods of treating cancer comprising, administering to a subject in need of treatment a composition comprising, a compound of structure A-L-C, or a pharmaceutically acceptable salt, prodrug, clathrate, tautomer or solvate thereof, wherein:

A is substituted or unsubstituted cycloalkyl, aryl, heteroaryl, heterocyclyl;

L is present or absent, if present L is a linker; and

C is substituted or unsubstituted cycloalkyl, aryl, heteroaryl, heterocyclyl, wherein at least one position is substituted with —B(OH)$_2$, and at least one position is substituted with alkoxy, alkoxydialkylamino or hydroxyl.

In some forms, A can be cycloalkyl, aryl, heteroaryl, heterocyclyl, L can be a linker or nothing, and C can be cycloalkyl, aryl, heteroaryl, heterocyclyl, wherein both meta positions of A relative to L can be —B(OH)$_2$, carboxylic acid, a mild lewis acid, a strong acid, or a weak acid, hydroxyl, or C1-C4 alkoxy and wherein the para position of C relative to L can be —B(OH)$_2$, carboxylic acid, a mild lewis acid, a strong acid, or a weak acid, hydroxyl, or C1-C4 alkoxy, and wherein zero or more remaining reactive positions on A and C can be a halogen.

In some forms A can be substituted phenyl.

In some forms L can be a linker. In some forms L is present or absent.

In some forms, C can be substituted phenyl.

In some forms, structure A-L-C can have the structure or wherein:

$R^1$, $R^2$, $R^3$, $R^4$, $R^5$, $R^6$, $R^7$, $R^8$, $R^9$ and $R^{10}$ can independently be hydrogen, —B(OH)$_2$, mild lewis acid, strong acid, weak acid, alkyl, alkenyl, alkynyl, halo, alkoxy, amino, alkylamino, dialkylamino, cyano, nitro, formyl, carboxyl, alkoxycarbonyl, aminocarbonyl, alkylaminocarbonyl, dialkylamino carbonyl, haloalkyl, haloalkloxy, haloalkylamino, di(haloalkyl)amino or sugars;

$R^8$ and $R^9$ can optionally be cyclized to form cycloalkyl, aryl, heteroaryl or heterocyclyl, which can optionally be substituted with —B(OH)$_2$, mild lewis acid, strong acid, weak acid, alkyl, alkenyl, alkynyl, halo, alkoxy, amino, alkylamino, dialkylamino, cyano, nitro, formyl, carboxyl, alkoxycarbonyl, aminocarbonyl, alkylaminocarbonyl, dialkylamino carbonyl, haloalkyl, haloalkloxy, haloalkylamino, di(haloalkyl)amino or sugars;

L can be present or absent, if present L can be C$_1$-C$_6$ alkyl, C$_2$-C$_6$ alkenyl, aryl, heteroaryl, cycloalkyl, heterocyclyl, -P-Q-S-, wherein P can be C$_1$-C$_6$ alkyl, C$_2$-C$_6$ alkenyl, aryl, heteroaryl, cycloalkyl or heterocyclyl, Q can be —N(R$^{11}$)—, —O—, —S—, —C(O)—, wherein R$^{11}$ can be hydrogen or C$_1$-C$_3$ alkyl, S can be present or absent, if present S can be C$_1$-C$_6$ alkyl, C$_2$-C$_6$ alkenyl, aryl, heteroaryl, cycloalkyl or heterocyclyl.

In some forms, $R^1$, $R^2$, $R^4$, $R^5$, $R^6$, $R^8$, and $R^{10}$ can independently be H, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl.

In some embodiments, the boronic acid analogs can be

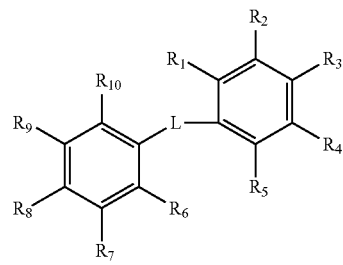

or the pharmaceutically acceptable salt or ester thereof, wherein $R^1$, $R^2$, $R^3$, $R^4$, $R^5$, $R^6$, $R^7$, $R^8$, $R^9$ and $R^{10}$ can independently be H, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl, boronic acid;

wherein the L is a linker and can be absent or present.

In some embodiments, L is present and is C$_1$-C$_6$ alkyl, C$_2$-C$_6$ alkenyl, aryl, heteroaryl, cycloalkyl, heterocyclyl, -P-Q-S-, wherein P is C$_1$-C$_6$ alkyl, C$_2$-C$_6$ alkenyl, aryl, heteroaryl, cycloalkyl or heterocyclyl, Q is —N(R$^{11}$)—, —O—, —S—, —C(O)—, wherein R$^{11}$ is hydrogen or C$_1$-C$_3$ alkyl, S is present or absent, if present S is C$_1$-C$_6$ alkyl, C$_2$-C$_6$ alkenyl, aryl, heteroaryl, cycloalkyl or heterocyclyl.

In some forms, $R^2$ can be —B(OH)$_2$, hydroxyl or C$_1$-C$_3$ alkoxy. In some forms, $R^2$ can be —B(OH)$_2$ or C$_1$ alkoxy. In some forms, $R^2$ can be —B(OH)$_2$.

In some forms, $R^1$, $R^4$, $R^5$, $R^6$, $R^{10}$ can be hydrogen.

In some forms, $R^3$, $R^7$, $R^8$, and $R^9$ can independently be hydrogen or C$_1$-C$_3$ alkoxy. In some forms $R^3$, $R^7$, $R^8$, and $R^9$ can be hydrogen. In some forms, $R^3$, $R^7$, $R^8$, and $R^9$ can be C$_1$ alkoxy.

In some forms, $R^3$, $R^7$, $R^8$, and $R^9$ can independently be hydrogen, —B(OH)$_2$, hydroxyl, C$_1$-C$_3$ alkoxy or C$_1$-C$_3$ alkoxydialkylamino. In some forms, $R^3$, $R^7$, $R^8$, and $R^9$ can independently be hydroxyl, C$_1$-C$_3$ alkoxy or C$_1$-C$_3$ alkoxydialkylamino. In some forms, $R^3$, $R^7$, $R^8$, and $R^9$ can be identical moieties. In some forms, $R^3$, $R^7$, $R^8$, and $R^9$ can be different moieties. In some forms, $R^3$, $R^7$, $R^8$, and $R^9$ can be C$_1$ alkoxy. $R^3$, $R^7$, $R^8$, and $R^9$ can be hydroxyl.

In some forms, $R^2$ can be —B(OH)$_2$, hydroxyl or C$_1$-C$_3$ alkoxy; $R^1$, $R^4$, $R^5$, $R^6$, $R^{10}$ can independently be hydrogen or C$_1$-C$_3$ alkoxy; $R^3$, $R^7$, $R^8$, and $R^9$ can independently be hydrogen, —B(OH)$_2$, hydroxyl, C$_1$-C$_3$ alkoxy or C$_1$-C$_3$ alkoxydialkylamino; and $R^8$ can be hydrogen or C$_1$-C$_3$ alkoxy.

In some forms, L can be absent.

In some forms, L can be present. In some forms L can be C$_1$-C$_6$ alkyl, C$_2$-C$_6$ alkenyl, aryl, heteroaryl, cycloalkyl, heterocyclyl, -P-Q-S-, wherein P can be C$_1$-C$_6$ alkyl, C$_2$-C$_6$ alkenyl, aryl, heteroaryl, cycloalkyl or heterocyclyl, Q can be —N(R$^{11}$)—, —O—, —S—, —C(O)—, wherein R$^{11}$ can be hydrogen or C$_1$-C$_3$ alkyl, S can be present or absent, if present S can be C$_1$-C$_6$ alkyl, C$_2$-C$_6$ alkenyl, aryl, heteroaryl, cycloalkyl or heterocyclyl. In some forms, L can be C$_2$-C$_6$ alkenyl. In some forms L can be comprise —C(O)—. In some forms L can comprise $C_3$-$C_6$ cycloalkyl. In some forms L can comprise $C_2$-$C_6$ alkenyl and —C(O)—. In some forms, L can comprise $C_2$-$C_5$ heterocyclyl. In some forms, L can comprise $C_1$-$C_6$ alkyl and aryl, heteroaryl, cycloalkyl or heterocyclyl. In some forms, L can comprise $C_2$ alkenyl. In some forms, L can be:

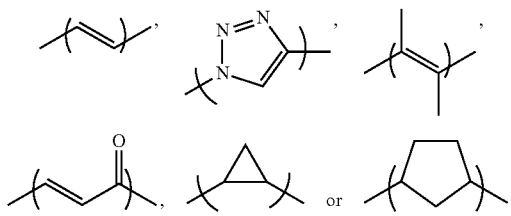

In some forms, the structure A-L-C can be:

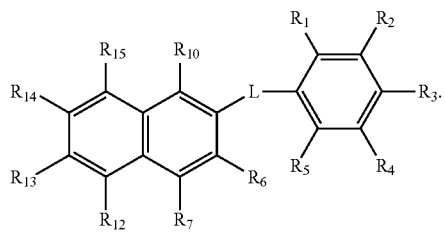

In some forms, $R^{12}$, $R^{13}$, $R^{14}$ and $R^{15}$ can independently be hydrogen, —B(OH)$_2$, mild lewis acid, strong acid, weak acid, alkyl, alkenyl, alkynyl, halo, alkoxy, amino, alkylamino, dialkylamino, cyano, nitro, formyl, carboxyl, alkoxycarbonyl, aminocarbonyl, alkylaminocarbonyl, dialkylamino carbonyl, haloalkyl, haloalkloxy, haloalkylamino, di(haloalkyl)amino or sugars. In some forms $R^{13}$ and $R^{15}$ can be hydrogen. In some forms $R^{12}$ and $R^{14}$ can independently be —B(OH)$_2$, hydroxyl, $C_1$-$C_3$ alkoxy or $C_1$-$C_3$ alkoxydialkylamino.

In some forms, $R^{13}$ and $R^{15}$ can be hydrogen and $R^{12}$ and $R^{14}$ can independently be —B(OH)$_2$, hydroxyl, $C_1$-$C_3$ alkoxy or $C_1$-$C_3$.

In some forms, structure A-L-C can have the structure:

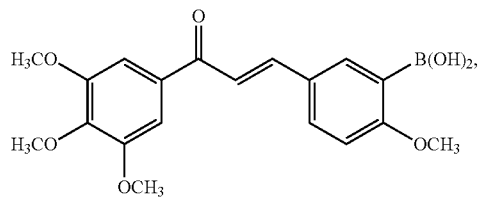

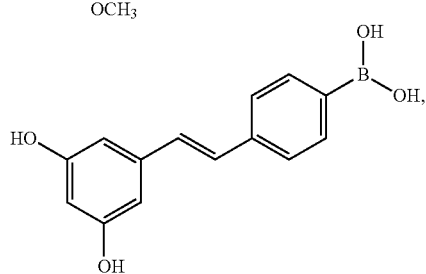

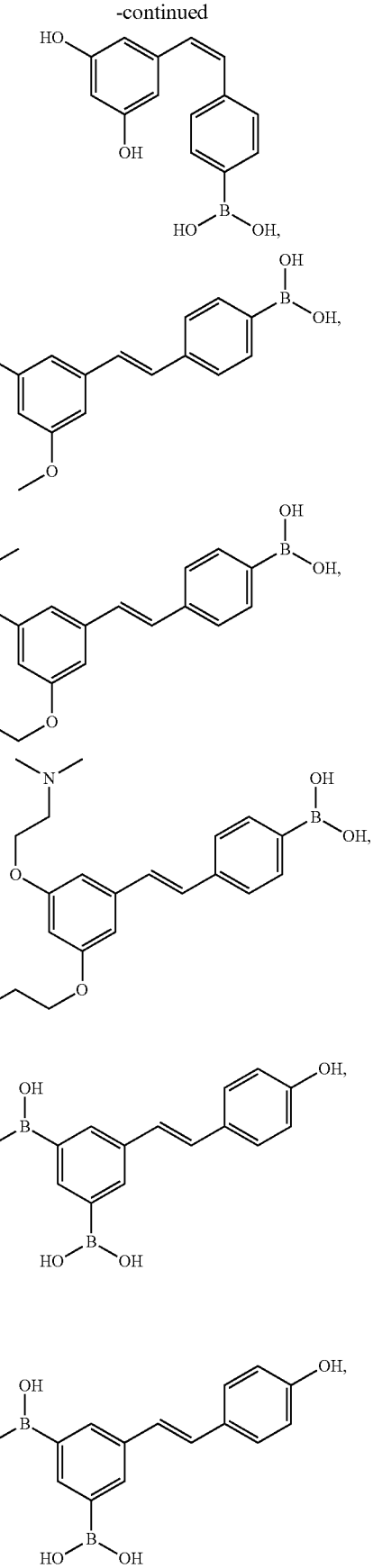

-continued

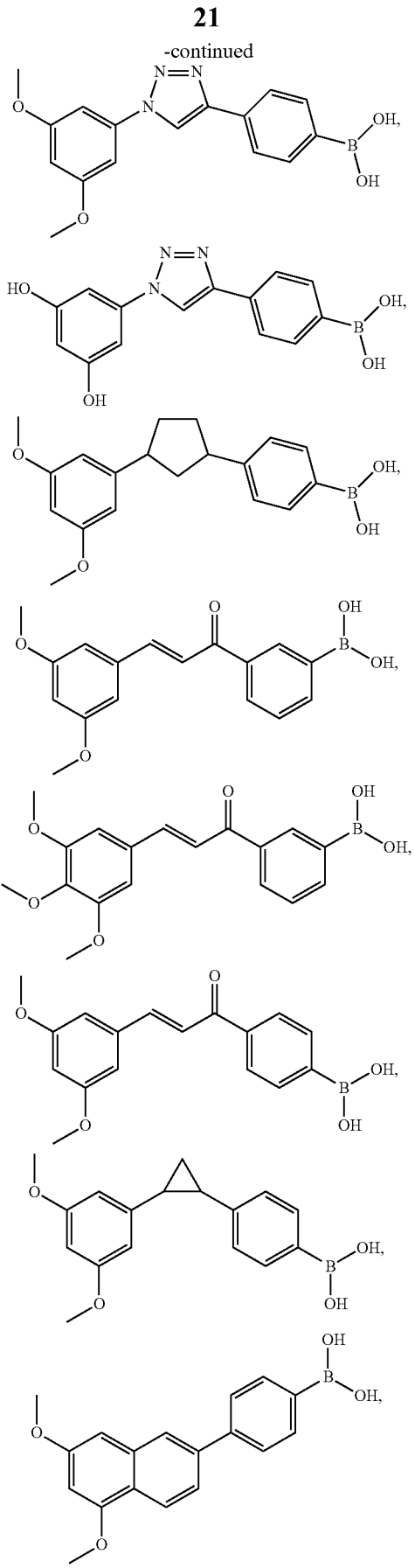

-continued

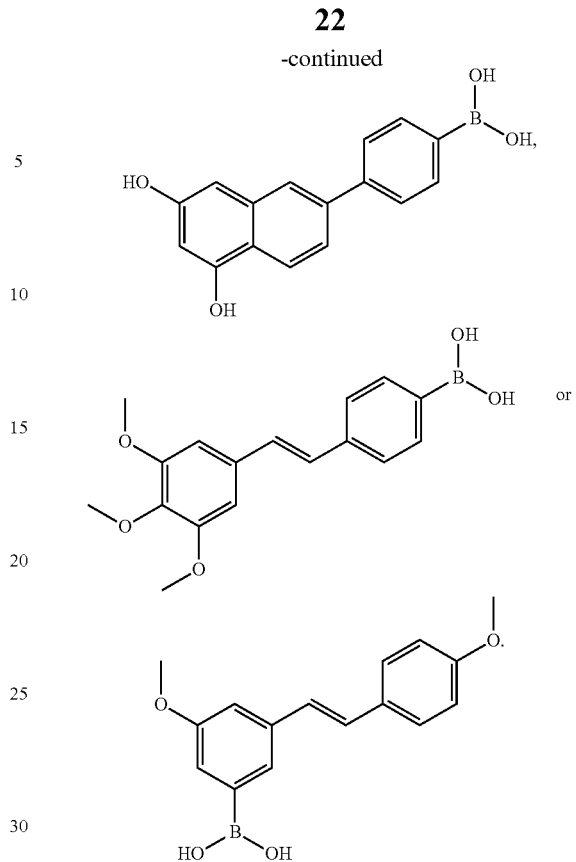

In some forms the compound can be trans. In some forms the compound can be cis. In some forms the compound is isolated trans. In some forms the compound can be isolated cis.

In some forms, the subject could have been assayed for cancer or a risk of cancer. In some forms, the subject can be at risk of having cancer. In some forms, the subject could have been diagnosed with cancer. In some forms, the cancer can be any cancer expressing a deacetylase enzyme. In some forms, the cancer can be prostate cancer, colon cancer, or breast cancer. In some forms, the subject can be assayed for the presence of cancer following administration of the composition.

In some forms, the composition can be administered in a therapeutically effective amount. In some forms, the composition can comprise a pharmaceutically acceptable carrier.

Disclosed are compounds having the structure A-L-C. In certain embodiments, A is cycloalkyl, aryl, heteroaryl, heterocyclyl, L is a linker or nothing, and C is cycloalkyl, aryl, heteroaryl, heterocyclyl.

In compounds 3 and 4, $R^2$ is where the boronic acid would go.

In certain embodiments, for Compound 3:

$R^1$, $R^2$, $R^3$, $R^4$, $R^5$, $R^6$, $R^7$, $R^8$, $R^9$ and $R^{10}$ can independently be H, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl.

While $R^2$, can be a functional group as described, $R^2$ is preferably boronic acid ($B(OH)_2$), carboxylic acid, a mild lewis acid, a strong acid, or a weak acid. In certain embodiments, $R^2$ is boronic acid.

While $R^7$ and $R^9$ can independently be a functional group as described for $R^1$, $R^7$ and $R^9$ in certain embodiments can be boronic acid ($B(OH)_2$), carboxylic acid, a mild lewis acid, a strong acid, or a weak acid. In certain embodiments, $R^7$ and $R^9$ are a hydroxyl.

In certain embodiments, the linker is not necessarily present. Boronic acid is a weak/mild Lewis acid, and can be changed for other like acids (carboxylic acid, etc.). In certain embodiments, boronic acid and hydroxyl groups can be $R^3$ and $R^4$. Click chemistry can be used for linking A and L.

Disclosed are compounds comprising, a structure A-L-C, wherein A is cycloalkyl, aryl, heteroaryl, heterocyclyl, L is a linker or nothing, and C is cycloalkyl, aryl, heteroaryl, heterocyclyl, wherein both meta positions of A relative to L are boronic acid ($B(OH)_2$), carboxylic acid, a mild lewis acid, a strong acid, or a weak acid, hydroxyl, or $C_1$-$C_4$ alkoxy and wherein the para position of C relative to L is preferably boronic acid ($B(OH)_2$), carboxylic acid, a mild lewis acid, a strong acid, or a weak acid, hydroxyl, or $C_1$-$C_4$ alkoxy, and wherein zero or more remaining reactive positions on A and C can be a halogen.

Also disclosed are compounds, wherein the L is a $C_2$-$C_6$ alkenyl.

Also disclosed are compounds, wherein the structure comprises the structure

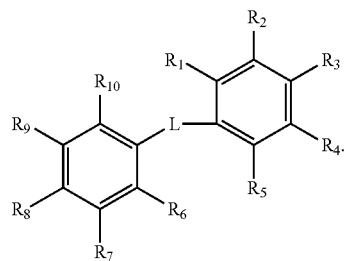

Disclosed are compounds, wherein $R^1$, $R^2$, $R^3$, $R^4$, $R^5$, $R^6$, $R^7$, $R^8$, $R^9$ and $R^{10}$ can independently be H, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl; wherein $R^2$ is boronic acid; wherein $R^3$, $R^7$, $R^8$, and $R^9$ are $C_1$-$C_3$ alkoxy; wherein the L is an alkenyl substituted with carbonyl; wherein $R^1$, $R^4$, $R^5$, $R^6$, and $R^{10}$ are hydrogen, and/or any combination or alone of these or any other characteristic disclosed herein.

Disclosed are compositions comprising any of the compounds disclosed herein.

Also disclosed are complexes comprising any of the compositions or compounds disclosed herein and a cell, wherein the cell expresses ER, wherein the cell is a cancer cell, wherein the cell is a breast cancer cell and/or any combination or alone of these or any other characteristic disclosed herein.

Disclosed are complexes comprising any of the compositions or compounds disclosed herein and ER or homolog, and/or any combination or alone of these or any other characteristic disclosed herein.

Also disclosed are methods comprising administering any of the compositions or compounds to a subject.

Disclosed are methods, wherein the subject has been assayed for cancer or a risk of cancer, wherein the subject has been treated for cancer, wherein the cancer expresses ER, wherein the cancer is breast cancer, wherein the subject is in need of treatment for cancer, wherein the subject is assayed for the presence of cancer following administration of the composition, and/or any combination or alone of these or any other characteristic disclosed herein.

The compounds disclosed herein also encompass pharmaceutically acceptable esters, amides, and salts of such compounds, as will be explained elsewhere herein.

The compounds also encompass pharmaceutically acceptable salts. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of the disclosed compounds to base used is chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds and accordingly can serve as prodrugs. Generally, these derivatives will be lower alkyl esters such as methyl, ethyl, and the like. Amide derivatives —(CO)NH_2, —(CO)NHR and —(CO)NR_2, where R is an alkyl group defined above, can be prepared by reaction of the carboxylic acid-containing compound with ammonia or a substituted amine.

Resveratrol, a natural product found in the skin of red grapes has received interest for potential anticancer activity. However, resveratrol has been reported to function as a mixed agonist/antagonist in estrogen-dependent breast cancer cell lines. WO 2011/022502 to Brown et al. discloses boronic acid analogs of resveratrol as clinical compounds related to breast cancer. Trans-boronic acid resveratrol showed more potent cytotoxic effects against estrogen dependent MCF-7 cells than resveratrol. Cell cycle and western blot analysis demonstrated that the trans analog inhibits the G1 cell cycle. This can explain the increased potency of the trans-boronic acid analog in MCF-7 cells as compare to resveratrol.

C. Formulation of Compositions

The compounds and compositions disclosed herein can be formulated in any useful way. Generally, the nature of the compound and the route of administration will influence the choice of formulation.

The deacetylase activators (also referred to herein as "active compounds") can be incorporated into pharmaceutical compositions suitable for administration. Such compositions typically comprise a pharmaceutically effective amount of a deacetylase activator and a pharmaceutically acceptable carrier. The pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

D. Therapeutic Uses

1. Activators of Deacetylase Enzymes

Histone deacetylases (HDACs) remove acetyl groups and lead to the compaction of the chromatin and the silencing of the DNA held inside. Often, these enzymes are associated with, or are actually part of, a transcription factor that binds to the DNA. Thus, the effects are often localized to given portions of the DNA, and the transacetylase/deacetylase enzymes modify the reading of only a small set of genes. HDACs also remove acetyl groups from various cellular proteins and regulate their stabilities and/or activities. Recent research has shown that these enzymes are good targets for cancer chemotherapy. Since these enzymes play such a central role in cellular function, we might expect that histone deacetylases or acetyltransferases would be too sensitive for use in therapy—that the drugs would attack all cells indiscriminately, leading to severe side effects.

More than 50% of human cancers possess mutations of p53. Deacetylation of p53 or mtp53 is dependent on SIRT1 activity. SIRT1 is significantly elevated in human prostate cancer, acute myeloid leukemia, and primary colon cancer (Deng, Int J Biol Sci, 2009, 147-152). Overexpression of SIRT1 is frequently observed in all kinds of non-melanoma skin cancers including squamous cell carcinoma, basal cell carcinoma, Bowen's disease, and actinic keratosis. In contrast, SIRT1 expression is reduced in many other types of cancers, including glioblastoma, bladder carcinoma, prostate carcinoma and ovarian cancers as compared to the corresponding normal tissues (Deng). Analysis of 44 breast cancer and 263 hepatic carcinoma cases also revealed reduced expression of SIRT1 in these tumors. It was realized that SIRT1 can act as both a tumor suppressor and a tumor promoter (oncogene).

Deng discusses several recent studies that provide convincing evidence that SIRT1 serves as a tumor suppressor. For example, Firestein et al. (PLoS ONE, 3:e2020, 2008) demonstrated that overexpression of SIRT1 in APCmin/+ mice reduces, instead of increases, colon cancer formation. The data demonstrated that the reduction in tumor development is caused by the ability of SIRT1 to deacetylate β-catenin and promote cytoplasmic localization of the nuclear-localized oncogenic form of β-catenin. Their further analysis also uncovered a significant inverse correlation between the presence of nuclear SIRT1 and the oncogenic form of β-catenin in 81 human colon tumor specimens analyzed. Ectopic over-expression of SIRT1 also greatly reduces cell proliferation in a human colon cancer cell line whose growth is driven by active β-catenin.

Wang et al. (Mol Cell. 2008, 32:11-20) found that SIRT1 expression is much lower in the BRCA1-associated breast cancer than BRCA1-wild type breast cancer in human. They further showed that BRCA1 binds to the SIRT1 promoter and positively regulates SIRT1 gene expression at both the mRNA and protein level, and that BRCA1 deficiency causes reduced SIRT1 levels, which may be responsible for the malignant transformation of BRCA1 mutant cells. Consistently, restoration of SIRT1 levels in BRCA1 mutant cancer cells inhibited proliferation of these cells in vitro and tumor formation in vivo when the cells were implanted into nude mice. In addition, resveratrol, which activates SIRT1 deacetylase activity, induced apoptosis in these cells and inhibited tumor formation. It was realized that SIRT1 not only acts as a tumor suppressor in the context of BRCA1 deficiency, but also that a SIRT1 activator, such as resveratrol, could serve as an excellent strategy for targeted therapy for BRCA1-associated breast cancer.

SIRT1 plays a role in DNA damage repair and in maintaining genome integrity (Deng, 2009). Analyzing SIRT1-deficient mice, Wang et al. found that Sirt1−/− embryos die at middle gestation stages, displaying increased acetylation of H3K9 and H4K16, reduced chromosome condensation, impaired heterochromatin formation, and abnormal mitosis. Sirt1−/− cells displayed chromosome aneuploidy and structural aberrations, conceivably originated from the continuous division of abnormal mitosis. SIRT1 deficiency also causes reduced ability to repair DNA-double strand breaks, radiation sensitivity, and impaired DDRs characterized by diminished γH2AX, BRCA1, RAD51 and NBS1 foci formation upon γ-irradiation. Thus, SIRT1 may play a role in recruiting these proteins to DNA damage sites.

In mammals, there are seven homologues of the sirtuin gene (SIRT1-7) that localize to the nucleus, cytoplasm, or mitochondria, and which utilize various substrates and exhibit a broad spectrum of functions (Kim et al., BMB Reports, 2008, 751-757). SIRT1 is the best-characterized mammalian Sir2 ortholog. This protein is involved in chromatin remodeling that culminates in gene silencing, DNA damage response, and an extended lifespan following calorie restriction (CR). Human SIRT6 deacetylates histone H3 lysine 9 (H3K9), which modulates telomeric chromatin. SIRT7 is a broadly expressed nucleolar protein that activates RNA polymerase I transcription and prevents apoptosis in response to stress response in the heart. Only SIRT2 is reported as a cytoplasmic protein; there it binds and deacetylates α-tubulin and interacts with HDAC6. SIRT2 also deacetylates histone H4 lysine 16 during mitosis. Overexpression of the SIRT2 suppresses adipogenesis in 3T3-L1 cells through the deacetylation of transcription factor FOXO1. The mitochondrial localization of SIRT3, SITT4, and SIRT5 is especially interesting because mitochondrial dysfunction is associated with both aging and cancer. SIRT3 is a mitochondrial deacetylase that regulates energy metabolism. SIRT4 is an ADP-ribosylase that plays an important role in pancreatic β-cells by inhibiting glutamate dehydrogenase activity. To date, the cellular substrate and biological role of SIRT5 remains unknown, although its structure suggests a deacetylase function. Based on these observations, sirtuins may provide beneficial effects in human diseases including, but are not limited to cancer, ageing, diabetes, and neuronal diseases.

Although several SIRT1 activating compounds have been recently developed (Howitz et al., Nature, 2003, 425:191-96; Nayagam et al., J Biomol Screen, 2006, 11:859-867; Milne et al., Nature, 2007, 450:712-716; and Minor et al., Sci Rep, 2011, 1:70), the effects of these compounds on human diseases have not yet been reported.

Disclosed herein are small molecule compounds (also referred to herein as "deacetylase activators") that activate SIRT1 enzyme activity. The disclosed compounds also reduce acetylation of mtp53 and depleted the level of mtp53. Additionally, the compounds disclosed herein reduce the acetyl-α-tubulin (K40) and the level of α-tubulin in cells.

In some embodiments, the compounds can treat a disease or condition associated with expression of a deacetylase enzyme. In some embodiments, the deacetylase enzyme is SIRT1.

In some embodiments, the compounds can treat a subject diagnosed with colon cancer, breast cancer, or prostate cancer.

In some embodiments, the compounds can treat a subject diagnosed with colon cancer or prostate cancer.

In some embodiments, the compounds can treat a subject diagnosed with prostate cancer.

In some embodiments, the compounds can treat a subject diagnosed with breast cancer.

In some embodiments, the compounds can treat a subject diagnosed with triple-negative breast cancer.

In some embodiments, the compounds can treat a subject diagnosed with cardiovascular disease.

In some embodiments, the compounds can treat a subject diagnosed with obesity.

In some embodiments, the compounds can treat a subject diagnosed with diabetes.

In some embodiments, the compounds can treat a subject diagnosed with a neurodegenerative disease. In some embodiments, the neurodegenerative disease is Alzheimer or Parkinson disease.

In some embodiments, the compounds can treat a subject diagnosed with inflammation.

In some forms, the compounds can treat a subject diagnosed with cancer, where cells of the cancer express mutant p53.

In some forms, the compounds can treat a subject diagnosed with cancer, where cells of the cancer overexpress mutant p53.

In some forms, the compounds can treat a subject diagnosed with cancer, where cells of the cancer under-express SIRT1.

In some forms, the compounds can treat a subject diagnosed with cancer, where cells of the cancer have low SIRT1 activity.

In some forms, the compounds can treat a subject at risk for age-related cancer.

In some forms, the compounds can treat a subject at risk for age-related cancer, where cells of the cancer express mutant p53, compositions and methods relate to treatment to reduce the risk of age-related cancers in subjects the cells of which express mutant p53.

Effective dosages and schedules for administering the compositions may be determined empirically, and making such determinations is within the skill in the art. The dosage ranges for the administration of the compositions are those large enough to produce the desired effect in which the symptoms disorder is affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 ng/kg to up to 100 mg/kg of body weight or more per day, depending on the factors mentioned above.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

Following administration of a disclosed composition, such as an antibody, for treating, inhibiting, or preventing a cancer, such as prostate cancer, the efficacy of the therapeutic antibody can be assessed in various ways well known to the skilled practitioner.

The compositions that activate deacetylases may be administered as a therapy or prophylactically to patients or subjects who are at risk for diseases such as cancer, cardiovascular disease, and neurological diseases.

E. Methods of Treatment

The disclosed compounds and compositions can be administered in any manner or route suitable to the compound or composition and the formulation of the compound or composition. Such techniques are well-known and can be applied to the methods and compositions disclosed herein.

1. Administration

The compounds and pharmaceutical compositions described herein can be administered to the subject in a number of ways depending on whether local or systemic treatment is desired, and on the area to be treated. Generally, oral administration is preferred and is generally available for the compounds and compositions disclosed herein. However, a compound or pharmaceutical composition can also be administered to a subject vaginally, rectally, intranasally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. Parenteral administration can use a slow release or sustained release system such that a constant dosage is maintained.

2. Identification of Subjects

Prior to treatment, subjects to be treated can be identified by determining characteristics that indicate the suitability of the treatment for that subject. For example, the disclosed compounds and methods are particularly suited for subjects having cancer where cells of the cancer express mutant p53, under-express SIRT1, have low SIRT1 activity, or a combination. Thus, subjects can be tested for expression of mutant p53, under-expression of SIRT1, low SIRT1 activity, or a combination. Subjects where cells of the cancer express mutant p53, under-express SIRT1, have low SIRT1 activity, or a combination, can then be treated with a disclosed compound. Similarly, subjects not yet diagnosed with cancer can be tested for expression of mutant p53, under-expression of SIRT1, low SIRT1 activity, or a combination. Subjects having cells that express mutant p53, under-express SIRT1, have low SIRT1 activity, or a combination, can then be treated with a disclosed compound to reduce the risk of age-related cancer.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Targeting Mutant p53 by SIRT1 Activator YK-3-237 Inhibits the Proliferation of Triple Negative Breast Cancer Cells General
Cell Culture and Reagents The SUM149PT and SUM1315MO2 cell lines were purchased from Asterand (Detroit, Mich.) and maintained as recommended. All other cell lines were obtained from American Type Cell Culture Collection (Manassas, Va.) or from the Tissue Culture Shared Resource of Georgetown University Medical Center. MCF7, MDA-MB-231, and T47D were maintained in Dulbecco's Modified Eagle Medium (DMEM) containing 5% heat inactivated fetal bovine serum (HI-FBS; HyClone, Logan, Utah) and 100 units/ml penicillin/streptomycin. HCC1937 and ZR-75-1 cells were maintained in RPMI1640 containing 10% HI-FBS and 100 units/ml penicillin/streptomycin. MDA-MB-468, HS578T, BT549, MDA-MB-453, BT474, and SK-BR-3 cells were maintained DMEM containing 10% HI-FBS and 100 units/ml penicillin/streptomycin. Cell culture reagents were obtained from Lonza (Basel, Switzerland), Invitrogen (Carlsbad, Calif.), or Cellgro (Manassas, Va.). YK-3-237 was synthesized as described previously (Kong et al., Biorg. Med. Chem., 2010, 18:971-977) and dissolved in dimethyl sulfoxide (DMSO).

MTT (3-(4,5-Dimethylthiazol-2-yl)-2,5-diphenyltetrazolium bromide) Assay

Cell viability was measured by MTT assay. In brief, cells were counted by the Luna Automated Cell Counter (Logos Biosystems, Gyunggi-Do, Korea) and subcultured in 96-well plates. The day after subculture, cells were treated with increasing amount of YK-3-237 and further incubated for approximately 72 hr in triplicate. To measure the viable cells, 20 µl of 5 mg/ml MTT solution was added per 100 µl of growth media. After 2-4 hr incubation at 37° C., the media were removed and 150 µl/well of DMSO was added to dissolve the formazan. The absorbance was measured by ELx808 microplate reader (BioTek, Winooski, Vt.). Viable cells are presented as a percent of the control. The half maximal inhibitory concentration (EC50) was calculated by CompuSyn software V1.0 (ComboSyn, Paramus, N.J.). The relative sensitivity was calculated by equation of –Log 2[(EC50 of each cell line)/(EC50 of T47D)].

Small Interfering RNA (siRNA) Transfection

For siRNA transfection, cells were subcultured in 6-well plates with density of 0.6~1×105 cells/well. The day after subculture, 100 nM/well of siRNA was transfected by Lipofectamine 2000 reagent (Invitrogen) in serum free media. Four hours after transfection, equal volume of normal growth media was added to each well and the cells were further incubated for 3-days. The siRNAs were purchased from Dharmacon (Lafayette, Colo.) with following sequences: control-siRNA, 5'-GACGAGCGGCACGUG-CACAUU-3; and SIRT1-siRNA, 5'-CCACCUGAGUUG-GAUGAUA-3'.

In Vitro SIRT Assay

The Fluor-de-Lys-SIRT1 and SIRT2 deacetylase assay were performed as manufacturer's instruction (Enzo Life Sciences, Farmingdale, N.Y.). For competition assay, 50 µM of suramin was added to reaction.

p53 Reporter Gene Assay

Plasmid DNAs for reporter gene assay were obtained from following sources: SIRT1 and SIRT1 H363Y (dominant negative mutant) from Addgene (Cambridge, Mass.); Expression vector for WTp53 from Dr. B. Vogelstein; and p53-Luc from Promega (Madison, Wis.). MCF7 cells were transfected with p53-Luc reporter plasmid with expression vector for WTp53 in the presence or absence of SIRT1 expression vector by Lipofectamine 2000 (Invitrogen). Twenty-four hour after transfection, the cells were further treated with YK-3-237 for 24 hr and luciferase activity was measured according to manufacturer's instruction (Promega) using Victor2 plate reader (PerkinElmer, Waltham, Mass., USA) at the Genomics and Epigenomics Shared Resource of Georgetown University Medical Center and normalized to β-galactosidase activities.

Western Blot Analysis and Antibodies

Preparation of cell lysates and western blot analyses were performed. Antibodies were obtained from the following sources: Ac-p53 (K382; #2525), Ac-α-tubulin (K40; #3971), phospho-ACC (S78; #3661), and ACC (#3676) from Cell Signaling (Danvers, Mass.); PARP (#556494) from BD Pharmingen (San Jose, Calif.); p53 (V1003) from Biomeda (Foster City, Calif.); ERα (sc-543) and SIRT1 (sc-15404) from Santa Cruz (Santa Cruz, Calif.); α-tubulin, β-Actin (A1978), and horseradish peroxidase-conjugated secondary antibodies from Sigma (St. Louis, Mo.). Chemiluminescence reagent was obtained from Santa Cruz or Thermo Scientific (Rockford, Ill.).

Cell Cycle Analysis

Cells were treated with either DMSO or 1 µM of YK-3-237 for 24 hr. The attached cells were harvested by trypsinization and combined with floating cells in the culture media. After washing by phosphate-buffered saline, the cells were fixed with 70% ethanol at –20° C. Flow cytometric analysis was performed with a FACSCalibur flow cytometer (Becton-Dickinson, Calif.) at the Flow Cytometry and Cell Sorting Shared Resource at Georgetown University Medical Center.

Quantitative Real Time-PCR (qRT-PCR) Analysis qRT-PCR was performed with an Applied Biosystems-Prism Sequence Detector System 7700 at the Genomics and Epigenomics Shared Resource of Georgetown University Medical Center. The primers were used with following sequences: PUMA: forward, 5'-GAC CTC AAC GCA CAG TAC-3' (SEQ ID NO:1) and reverse, 5'-GCA TCT CCG TCA GTG CAC-3' (SEQ ID NO:2); NOXA: forward, 5'-TCC GGC AGA AAC TTC TGA AT-3 (SEQ ID NO:3) and reverse, 5'-TTC CAT CTT CCG TTT CCA AG-3' (SEQ ID NO:4).

Statistical Analysis

To compare two groups of interest, the two-tailed Student's t-test was applied for statistical analysis. * indicates $P<0.05$;  indicates $P<0.01$; and * indicates $P<0.001$.

Results

YK-3-237 Inhibits the Proliferation of TNBC Cells

Figure 1B:
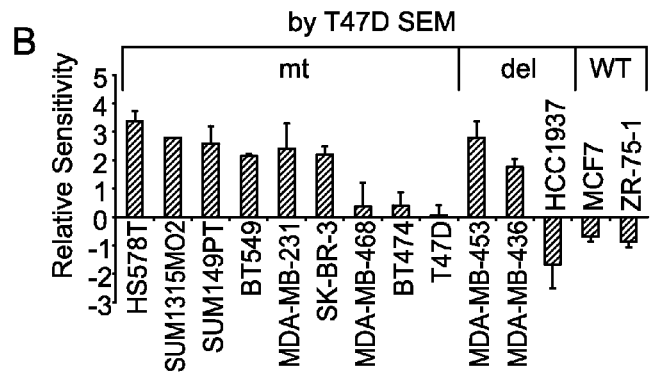
Figure 1C:
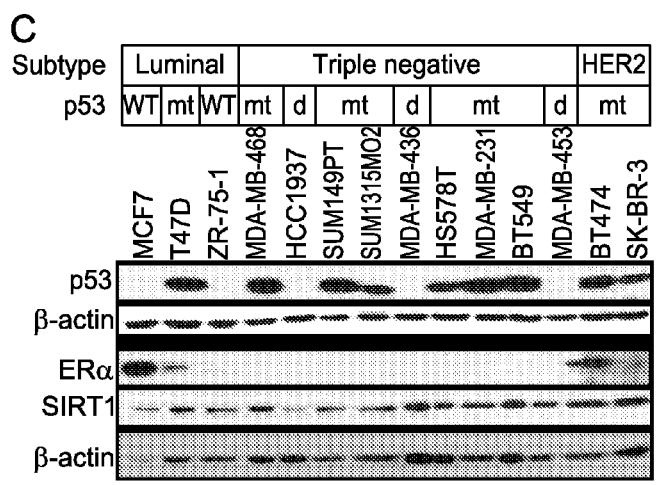
Figure 1D:
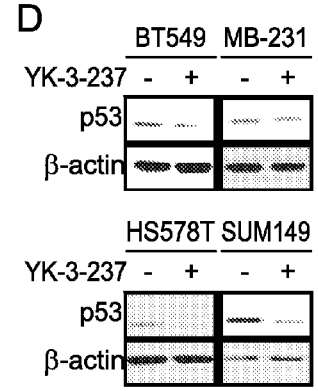
Figure 2:
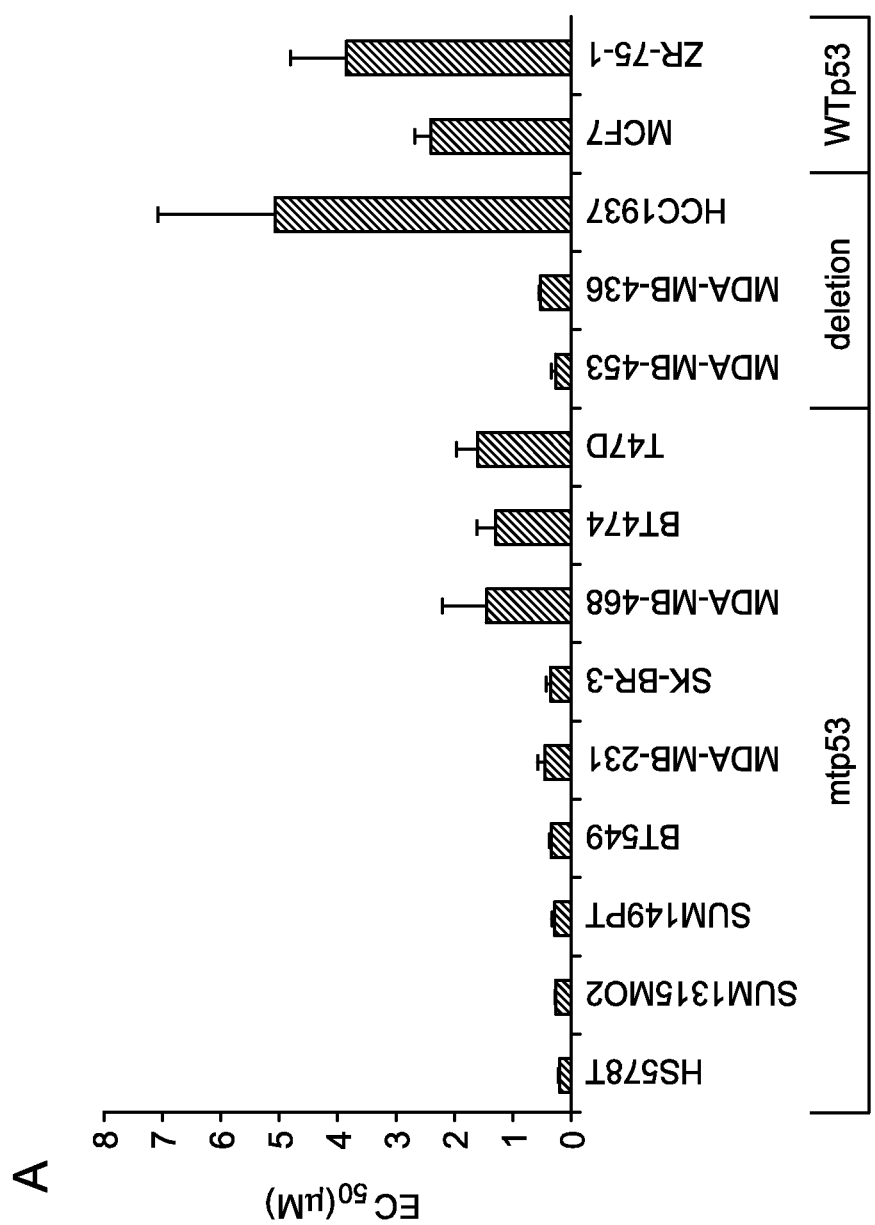
FIG. 2 is a bar graph showing breast cancer cells were treated with increasing amount of YK-3-237 for approximately 72 hr and the viable cells were measured by MTT assay. The EC$_{50}$ value of each cell line is presented as mean±SEM from two independent experiments performed in triplicate.

Previously it has been reported that YK-3-237 (FIG. 1A) exhibited potent anti-proliferative activity toward a broad range of NCI cancer cell lines with unknown mechanism (Kong et al., Biorg. Med. Chem., 2010, 18:971-97). Cell viability assay with a panel of breast cancer cell lines were performed to determine the anti-proliferative effects of YK-3-237. Cells were treated with increasing concentration of YK-3-237 up to 72 hr and viable cells were measured by MTT assay. Notably, YK-3-237 exhibited the anti-proliferative activities toward most of the breast cancer cell lines tested at submicromolar concentration (Table 1 and FIG. 2). As shown in FIG. 1B, YK-3-237 more preferentially inhibited the proliferation of breast cancer cell lines carrying mtp53. Most of triple negative breast cancer (TNBC) cell lines in this study are expressing mtp53 (Table 1). Western blot analysis showed that the levels of p53 protein are highly elevated in TNBC cell lines carrying mutations of p53 gene (FIG. 1C). Although cells with WTp53 such as MCF7 and ZR-75-1 expressed detectable levels of p53 protein (data not shown), the levels of mtp53 protein are much higher than that of WTp53. As expected, expression of ERα was not detected in TNBC cell lines (FIG. 1C). Notably, no significant difference in the level of SIRT1 protein was observed in our breast cancer cell line panel (FIG. 1C). To determine the effect of YK-3-237 on the level of mtp53, western blot analysis was further performed with cell lysates from TNBC cells treated with 1 µM of YK-3-237 for 24 hr. 24 hr treatment of 1 µM of YK-3-237 reduced the level of mtp53 protein in all TNBC cell lines tested (FIG. 1D).

TABLE 1 p53 status of breast cancer cell lines in this study.

| | Cell line | $EC_{50}$ ± SEM (µM) | p53 Status [Wasielewski, Breast Cancer Res Treat 99: 97-101 (2006)] |
|---|---|---|---|
| TNBC | HS578T | 0.160 ± 0.043 | V157F |
| | MDA-MB-453 | 0.241 ± 0.086 | Homozygous deletion (exon 10/11) |
| | SUM1315MO2 | 0.253 ± 0.028 | C135F |
| | SUM149PT | 0.289 ± 0.066 | M237I |
| | BT549 | 0.353 ± 0.017 | R249S |
| | MDA-MB-231 | 0.431 ± 0.136 | R280K |
| | MDA-MB-436 | 0.501 ± 0.062 | E204fsX45 (Del) |
| | MDA-MB-468 | 1.436 ± 0.754 | R273H |
| | HCC1937 | 5.031 ± 2.010 | R306X (Del) |

TABLE 1-continued p53 status of breast cancer cell lines in this study.

| | Cell line | $EC_{50} \pm$ SEM (µM) | p53 Status [Wasielewski, Breast Cancer Res Treat 99: 97-101 (2006)] |
|---|---|---|---|
| Luminal | T47D | $1.573 \pm 0.370$ | L194F |
| | MCF7 | $2.402 \pm 0.256$ | WT |
| | ZR-75-1 | $3.822 \pm 0.967$ | WT |
| HER2 | BT474 | $1.249 \pm 0.372$ | E285K |
| | SK-BR-3 | $0.346 \pm 0.066$ | R175H |

YK-3-237 Deacetylates Mtp53 in TNBC Cell Lines

Figure 1E:
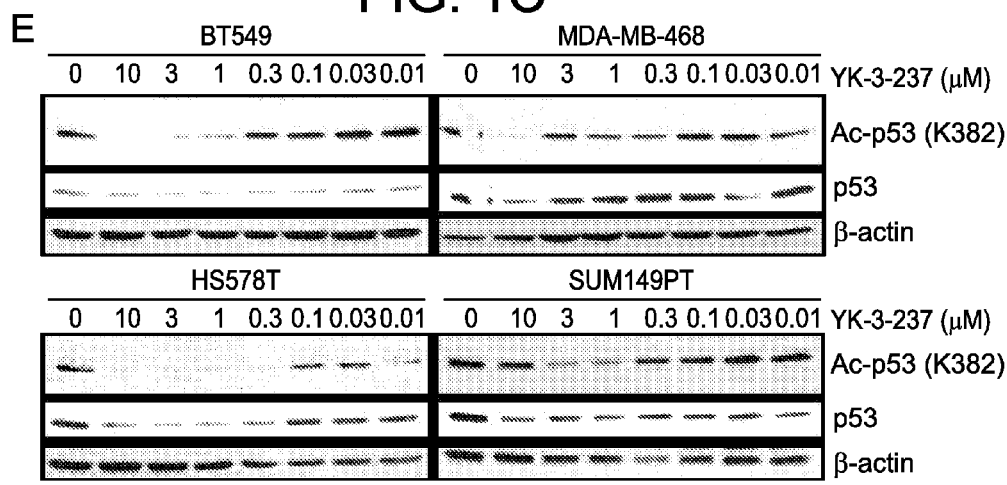
Figure 3A:
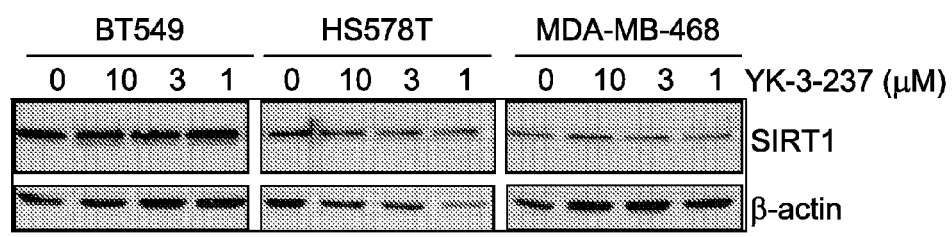
FIGS. 3A and 3B show the effect of compound YK-3-237 on the expression of SIRT1 protein and acetyl-mtp53 by western blot analysis with indicated antibodies.
Figure 3B:
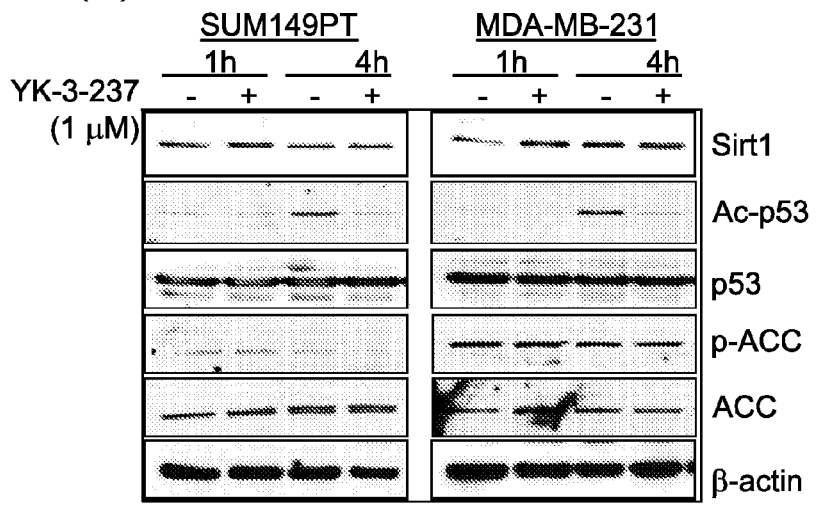

Previously it has been reported that the stability of WTp53 is post-translationally regulated by acetylation at K382 residue. Recently, mtp53 has also been reported to be regulated by acetylation. We analyzed the acetylation status of mtp53 in TNBC cell lines treated with YK-3-237 by western blot analysis. Twenty four hour treatment of YK-3-237 reduced both the acetylation at K382 residue and the level of mtp53 in a dose-dependent manner in mtp53 TNBC cell lines (FIG. 1E). It was also observed that treatment of YK-3-237 had little or no significant effect on the level of SIRT1, one of the deacetylases for p53, in mtp53 TNBC cell lines up to 10 µM (FIG. 3A). The deacetylation of mtp53 was observed as early as 4 hr after treatment of YK-3-237 without significant reduction of mtp53 level (FIG. 3B).

SIRT1 is a well-known deacetylase for p53 at K382 residue. We addressed whether YK-3-237 affects SIRT enzyme activity by in vitro SIRT assay with a fluorophore-conjugated peptide substrate. As shown in FIG. 4A, YK-3-237 activated SIRT1 enzyme activities in a dose-dependent manner. Under this condition, a SIRT1/2 inhibitor suramin antagonized YK-3-237-mediated SIRT1 activation. Interestingly YK-3-237 was more potent to activate SIRT1 activity than resveratrol and maximal activation was observed at 10 µM concentration (FIG. 5A). Moreover, YK-3-237 is much more potent to reduce the survival of SUM149PT cells than resveratrol in a long-term survival assay (FIG. 5B). YK-3-237 also activates SIRT2 enzyme in vitro and enhanced the deacetylation of α-tubulin (K40) in HS578T cells (FIGS. 5C and 5D).

To exclude potential artifacts from in vitro assay, we further confirmed SIRT1 activation by YK-3-237 using p53-Luc reporter gene assay (FIG. 4B-C). MCF7 cells were transfected with p53-Luc reporter plasmid and WTp53 expression vector in the presence or absence of SIRT1 or dominant negative (DN)-SIRT1 expression vector and further treated with YK-3-237. As expected, YK-3-237 repressed the WTp53-mediated activation of p53-Luc reporter gene in a dose-dependent manner (FIG. 4B, lanes 1-4). Under this condition, co-expression of SIRT1 reduced the p53-Luc reporter activity induced by WTp53 and co-treatment of YK-3-237 further enhanced the SIRT1-mediated repression of p53-Luc reporter (FIG. 4B, lanes 5-7). On the contrary, DN-SIRT1 did not repress the p53-mediated reporter gene activation. In addition, repression of p53-Luc reporter by YK-3-237 was limited in the presence of DN-SIRT1 (FIG. 4B, lanes 9 and 10). The effect of SIRT1 knockdown (SIRT1-KD) on the WTp53-mediated transcription was also tested in MCF7 cells. MCF7 cells were transfected by either control- or SIRT1-siRNA followed by transfection of p53-Luc and further treated with increasing amount of YK-3-237. Under this condition, SIRT1-KD slightly induced p53-Luc reporter activity (FIG. 4C). While YK-3-237 reduced p53-Luc reporter activity in control-siRNA-transfected cells, SIRT1-KD antagonized the YK-3-237-mediated repression of p53-Luc activity. These results suggest that the repression of WTp53 transcriptional activity by YK-3-237 is, at least partly, dependent on the presence of functional SIRT1.

SIRT1-dependent deacetylation of mtp53 was further investigated in two mtp53 cell lines, HS578T and SUM149PT. First, HS578T cells were pre-treated with 10 µM of suramin for 1 hr and further treated with 1 µM of YK-3-237 for 23 hr. As shown in FIG. 4D, pre-treatment of suramin reversed both deacetylation of mtp53 (K382) and reduction of mtp53 protein. Second, the effect of SIRT1-KD on the YK-3-237 activity was determined in SUM149PT cells. After transfection of either control- or SIRT1-siRNA, the cells were further treated with increasing amount of YK-3-237 for 4 hr. Under this condition, knockdown of SIRT1 increased acetyl-mtp53 in SUM149PT cells (FIG. 4E). In addition, knockdown of SIRT1 reversed deacetylation of mtp53 by YK-3-237 (FIG. 4E). Taken together, these results indicate that YK-3-237 activates the SIRT1 enzyme activity in vitro and deacetylates both wild type and mutant p53 in cells in a SIRT1-dependent manner.

YK-3-237 Induces WTp53-Target Gene Expression in TNBC Cell Lines Carrying mtp53

Figures 6A, 6B:
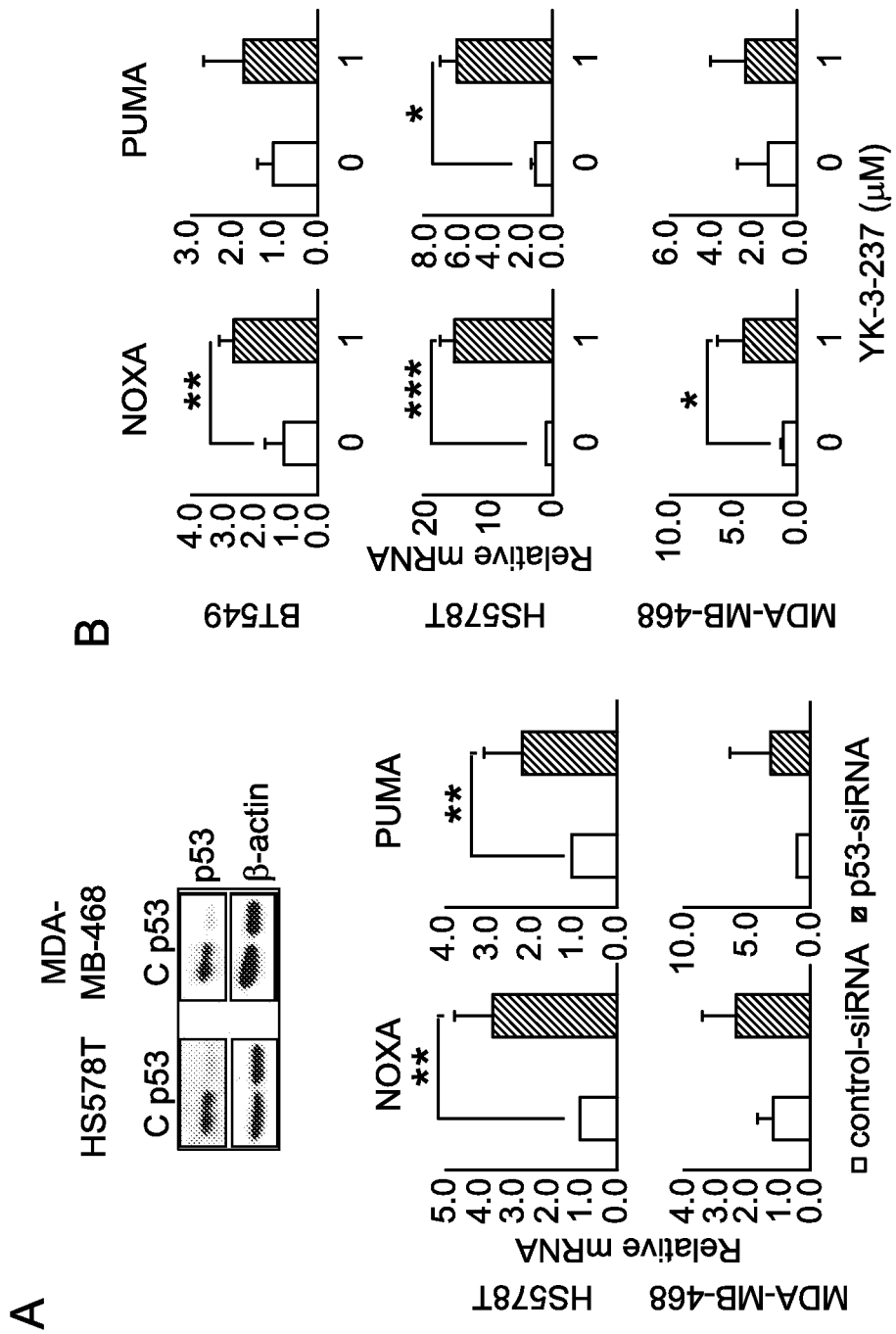
FIGS. 6A and 6B show the effect of mtp53 depletion and compound YK-3-237 on the expression of WTp53-target genes in TNBC cell lines.

Previously, it has been reported that mtp53 reduces p63/p73-mediated transcriptional activation of WTp53-target genes and knockdown of mtp53 activates WTp53-target gene expression in a cell type-specific manner. Consistently, knockdown of mtp53 in two TNBC cell lines, HS578T and MDA-MB-468, induced the mRNA expression of PUMA and NOXA (FIG. 6A). Quantitative real time-PCR analysis further confirmed the YK-3-237-mediated induction of WTp53-target genes, PUMA and NOXA in three different TNBC cell lines, BT549, HS578T, and MDA-MB-468 (FIG. 6B). These results indicate that the reduction of mtp53 level by YK-3-237-mediated deacetylation functionally and specifically releases transcriptional suppression of WTp53 target genes by mtp53 proteins in these cells.

YK-3-237 Induces Apoptotic Cell Death in TNBC Cells

Figure 7A:
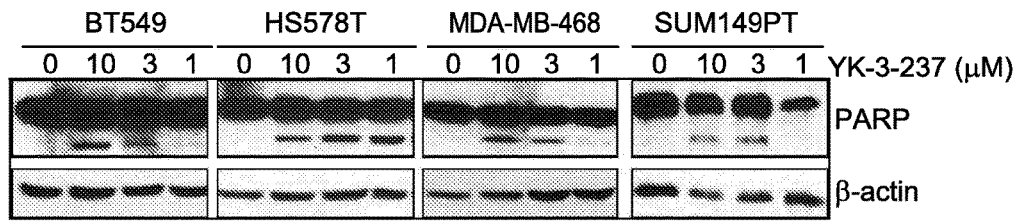
FIGS. 7A and 7B show the induction of apoptotic cell death and G2/M arrest by compound YK-3-237 in TNBC cell lines. Cells were treated with YK-3-237 for 24 hr and both floating and attached cells were harvested for western blot analysis (FIG. 7A) and cell cycle analysis (FIG. 7B).
Figure 7B:
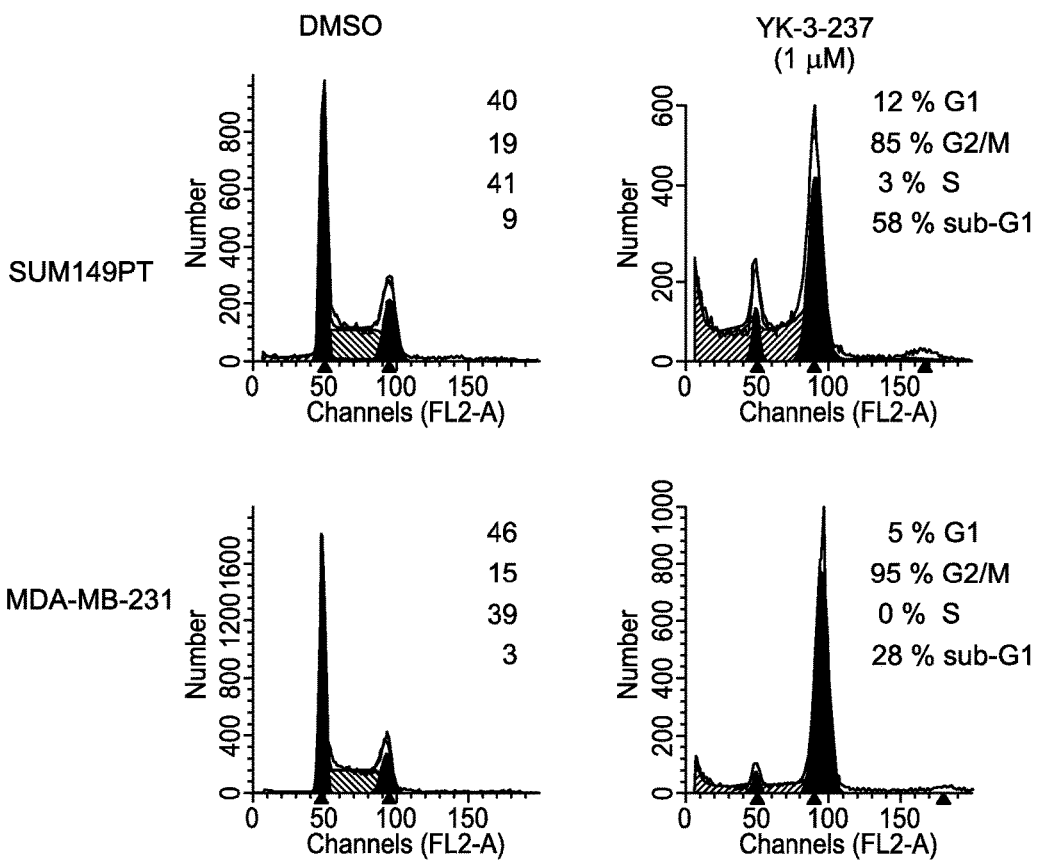

It has been well established that induction of WTp53 target genes arrests cells to G2 phase of cell cycle and finally leads cells to apoptotic cell death. In fact, YK-3-237 induced PARP cleavage, a hallmark of caspase-dependent apoptosis, within 24 hr post-treatment (FIG. 7A). TNBC cells treated with YK-3-237 were markedly arrested at G2/M phase (FIG. 7B). In addition, sub-G1 fractions were also drastically increased by YK-3-237 within 24 hr post-treatment in TNBC cells with mtp53 (FIG. 7B).

DISCUSSION

We demonstrated here a small molecule YK-3-237 to reduce the proliferation of a broad range of breast cancer cell lines carrying mtp53. YK-3-237 reduced the level of mtp53 by removing acetyl group from its K382 residue in a SIRT1-dependent manner. In addition, YK-3-237 activated in vitro enzyme activity of purified human SIRT1 more potently than resveratrol. In cells carrying WTp53, YK-3-237 enhanced SIRT1-mediated repression of transcriptional activation by WTp53. Similar to mtp53-KD, YK-3-237 induced mRNA expression of PUMA and NOXA and apoptotic cells death in TNBC cell lines.

The fact that more than 50% of human cancers possess mutations of p53 provides rationale for targeting mtp53s to treat human cancer. More importantly, active oncogenic potentials by gain-of-function of mtp53s stress this approach as a broad range therapeutic opportunity. Many attempts, however, have been limited by various characters of diverse mtp53. As examples, small molecules those restore wild-type conformation of mtp53 such as PRIMA-1, MIRA-1, CP-31398, and P53R3 have effects only on specific types of mtp53. More recently, a HSP90 inhibitor 17AAG has been suggested as an alternative approach to reduce the proliferation of broad range cancer cell lines carrying various mtp53. In this study, inhibiting HSP90 by 17AAG disrupts molecular chaperone complex to liberate mtp53 for degradation by MDM2.

The mechanism of hyperstabilization of mtp53 is largely unknown. The stabilization of p53 proteins are thought to be regulated by post-translational modifications. For WTp53, acetylation of K382 residue has been proposed as an important determinant to stabilize the WTp53 protein. Although mtp53 is known to be acetylated, the roles of these acetylations of mtp53 still need further investigation. Regardless of this, we demonstrated in this study that mtp53 is acetylated at K382 residue in TNBC cell lines and a small molecule compound YK-3-237 reduced this acetylation from mtp53 and depleted the level of mtp53. In addition, YK-3-237 activated SIRT1 enzyme activity in vitro and the deacetylation of either WTp53 or mtp53 was dependent on SIRT1 activity. This was demonstrated by overexpression of wild type or DN-SIRT1, SIRT1-KD, and SIRT1 inhibition by a small molecule inhibitor, regardless of mtp53 types. As reported recently, YK-3-237 could activate in vitro SIRT1 activity in the presence of aminomethylcoumarin (AMC)-tagged peptide derived from p53 protein. Contrarily, YK-3-237 could not activate in vitro SIRT1 activity toward nascent p53 peptide. Allosteric SIRT1 activator such as STAC-1 has been known to require specific hydrophobic motifs found in a subset of SIRT1 substrates including PGC-1α and FOXO3a to facilitate SIRT1 activation. To our knowledge, p53 has no such motifs. Notably, SRT1720 was reported to reduce acetyl-p53 in cells, in spite of the fact that it could not activate in vitro SIRT1 activity toward nascent p53 peptide.

As we demonstrated, YK-3-237 also activated in vitro enzyme activity of human SIRT2. Additionally, YK-3-237 reduced the acetyl-α-tubulin (K40) and the level of α-tubulin in cells. Because YK-3-237 was determined not to bind to tubulin in vitro, it is less plausible that YK-3-237 exerts its anti-proliferative effect through inhibition of tubulin polymerization. Rather, decrease of α-tubulin through deacetylation by SIRT2 may contribute to G2/M arrest in a cooperative manner with depletion of mtp53.

In summary, we demonstrated YK-3-237 as a small molecule activator of SIRT1. Activation of SIRT1 by YK-3-237 functionally reduces the level of mtp53 by deacetylation. Roles of SIRT1 in human cancers have been controversial and both SIRT1 inhibitors and activators (such as resveratrol) have been reported to inhibit growth of human cancer cell lines. Although several SIRT1 activating compounds have been recently developed, the anti-cancer effects of these compounds have not been reported. Because SIRT1 has a deacetylase activity against broad range of substrates that are acting as either tumor promoters or tumor suppressors, activating its enzyme activity can be beneficial for subtypes of cancers. Given SIRT1's involvement in many biological processes, including cancer, ageing, diabetes, and neuronal diseases, YK-3-237 represents a viable treatment for such biological processes and a valuable tool for basic research.

Those skilled in the art will recognize, or be able to ascertain using no more than routine experimentation, many equivalents to the specific embodiments of the method and compositions described herein. Such equivalents are intended to be encompassed by the following claims.

We claim:

1. A method comprising administering a composition to a subject, wherein the composition comprises a compound, or a pharmaceutically acceptable salt, prodrug, clathrate, tautomer or solvate thereof, wherein the compound has the structure:

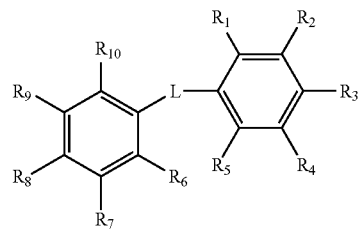

wherein $R^1$, $R^2$, $R^3$, $R^4$, $R^5$, $R^6$, $R^7$, $R^8$, $R^9$ and $R^{10}$ are independently hydrogen, hydroxyl, —B(OH)$_2$, alkyl, alkenyl, alkynyl, halo, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, or di(haloalkyl)amino;

$R^8$ and $R^9$ are optionally cyclized to form cycloalkyl, aryl, heteroaryl or heterocyclyl, optionally substituted with —B(OH)$_2$, mild Lewis acid, strong acid, weak acid, alkyl, alkenyl, alkynyl, halo, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, di(haloalkyl)amino or sugars;

L is

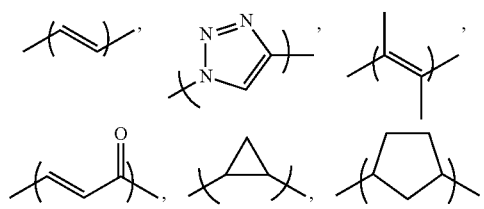

or L is absent when $R^8$ and $R^9$ are cyclized;

wherein at least one of $R^1$, $R^2$, $R^3$, $R^4$, $R^5$, $R^6$, $R^7$, $R^8$, $R^9$, and $R^{10}$ is or includes —B(OH)$_2$, and at least one of $R^1$, $R^2$, $R^3$, $R^4$, $R^5$, $R^6$, $R^7$, $R^8$, $R^9$, and $R^{10}$ is or includes alkoxy, alkoxydialkylamino or hydroxyl, wherein the compound is a deacetylase activator, wherein the subject is in need of treatment of a disease or condition, wherein the disease or condition is associated with expression of a deacetylase enzyme, and wherein cells of the subject express mutant p53, underexpress SIRT1, have low SIRT1 activity, or combinations thereof.

2. The method of claim 1, wherein:

$R^1$, $R^4$, $R^5$, $R^6$, $R^7$, $R^8$, $R^9$, and $R^{10}$ are independently hydrogen, —B(OH)$_2$, alkyl, alkenyl, alkynyl, halo, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, or di(haloalkyl)amino; and $R^8$ and $R^9$ are optionally cyclized to form cycloalkyl, aryl, heteroaryl or heterocyclyl, optionally substituted with —B(OH)$_2$, mild Lewis acid, strong acid, weak acid, alkyl, alkenyl, alkynyl, halo, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, di(haloalkyl)amino or sugars.

3. The method of claim 1, wherein $R^2$ is —B(OH)$_2$, hydroxyl or $C_1$-$C_3$ alkoxy.

4. The method of claim 1, wherein L is present and is:

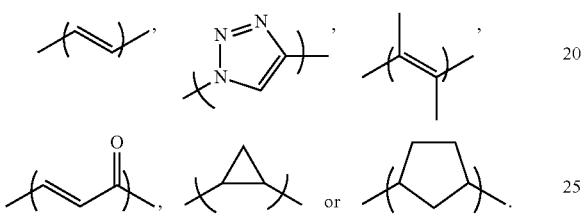

5. The method of claim 1, wherein L is absent.

6. The method of claim 1, having the structure

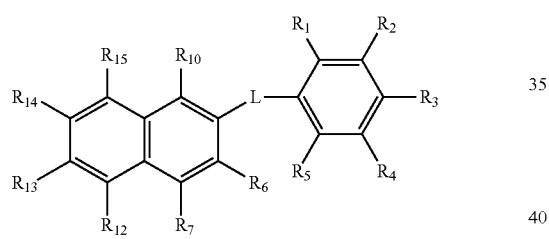

wherein:

$R^{12}$, $R^{13}$, $R^{14}$ and $R^{15}$ are independently hydrogen, hydroxyl, —B(OH)$_2$, alkyl, alkenyl, alkynyl, halo, alkoxy, amino, alkylamino, dialkylamino, cyano, nitro, formyl, carboxyl, alkoxycarbonyl, alkoxydialkylamino, aminocarbonyl, alkylaminocarbonyl, dialkylamino carbonyl, haloalkyl, haloalkloxy, haloalkylamino, or di(haloalkyl)amino.

7. The method of claim 6 wherein, $R^{13}$ and $R^{15}$ are hydrogen and $R^{12}$ and $R^{14}$ are independently —B(OH)$_2$, hydroxyl, $C_1$-$C_3$ alkoxy or $C_1$-$C_3$ alkoxydialkylamino.

8. The method of claim 1, wherein the compound has the structure:

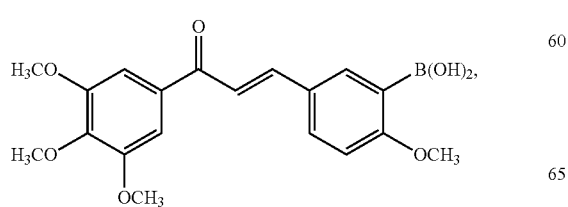

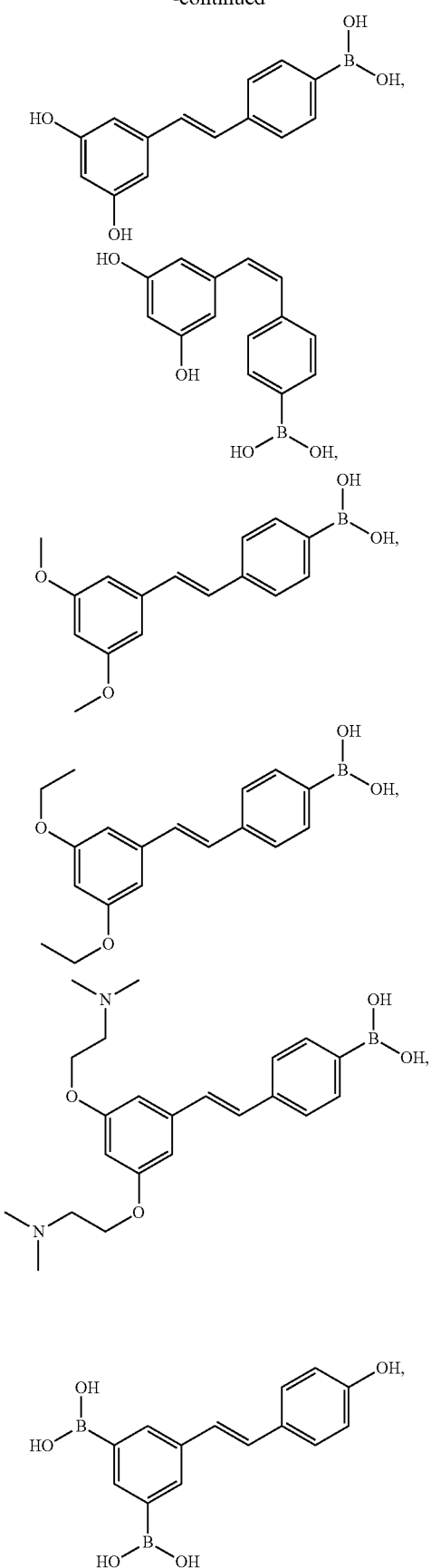

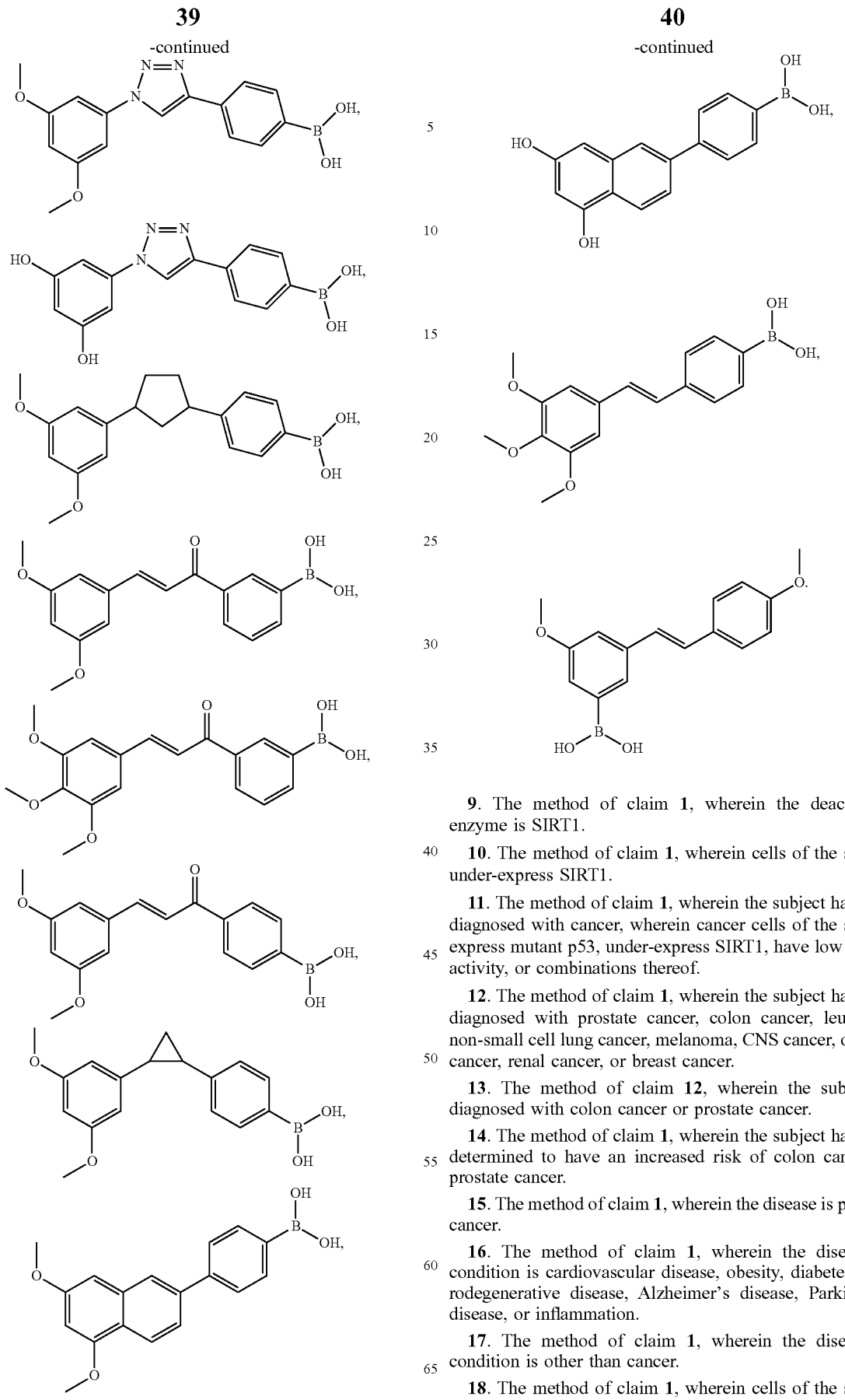

9. The method of claim 1, wherein the deacetylase enzyme is SIRT1.

10. The method of claim 1, wherein cells of the subject under-express SIRT1.

11. The method of claim 1, wherein the subject has been diagnosed with cancer, wherein cancer cells of the subject express mutant p53, under-express SIRT1, have low SIRT1 activity, or combinations thereof.

12. The method of claim 1, wherein the subject has been diagnosed with prostate cancer, colon cancer, leukemia, non-small cell lung cancer, melanoma, CNS cancer, ovarian cancer, renal cancer, or breast cancer.

13. The method of claim 12, wherein the subject is diagnosed with colon cancer or prostate cancer.

14. The method of claim 1, wherein the subject has been determined to have an increased risk of colon cancer or prostate cancer.

15. The method of claim 1, wherein the disease is prostate cancer.

16. The method of claim 1, wherein the disease or condition is cardiovascular disease, obesity, diabetes, neurodegenerative disease, Alzheimer's disease, Parkinson's disease, or inflammation.

17. The method of claim 1, wherein the disease or condition is other than cancer.

18. The method of claim 1, wherein cells of the subject have low SIRT1 activity.

19. The method of claim 1, wherein the compound has the structure:
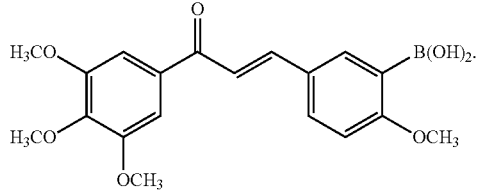 [SMILES: COc1ccc(/C=C/C(=O)c2cc(OC)c(OC)c(OC)c2)cc1B(O)O]
20. The method of claim 1, wherein when $R_2$ or $R_4$ is —B(OH)$_2$, $R_3$ is not alkoxy, and wherein when $R_7$ or $R_9$ is —B(OH)$_2$, $R_8$ is not alkoxy.
21. The method of claim 20, wherein the compound has the structure:
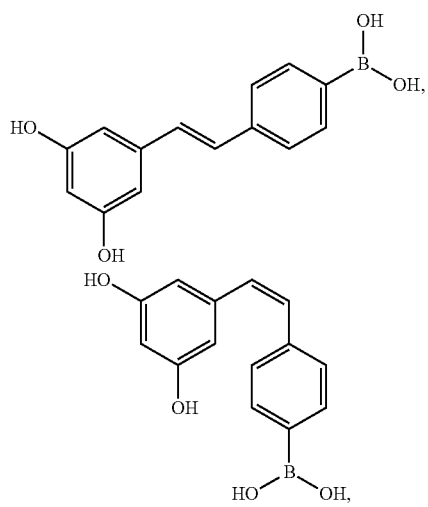
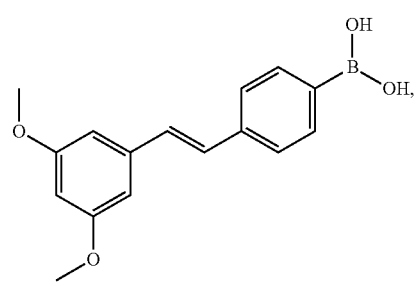
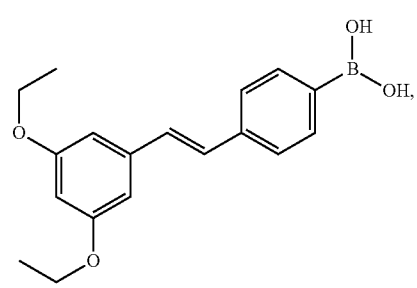
-continued
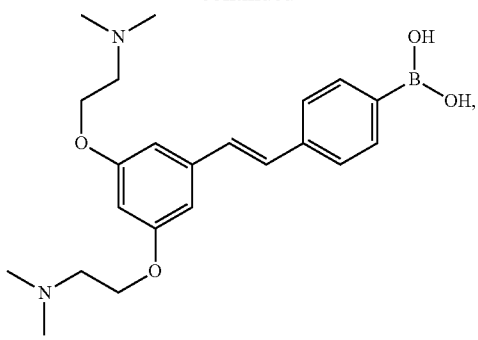
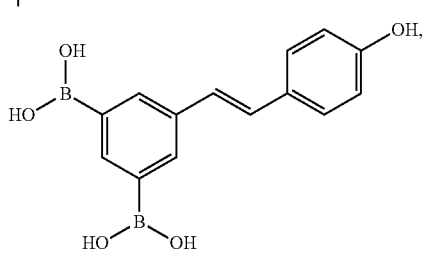
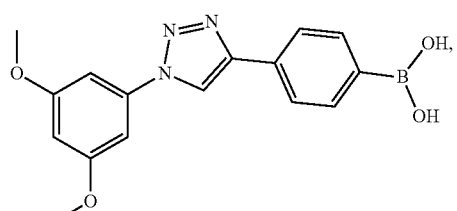
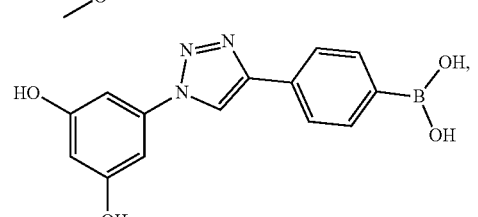
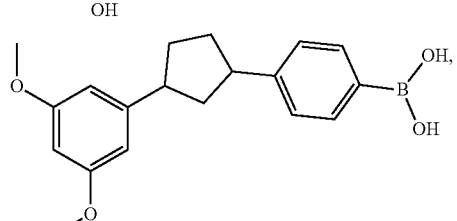
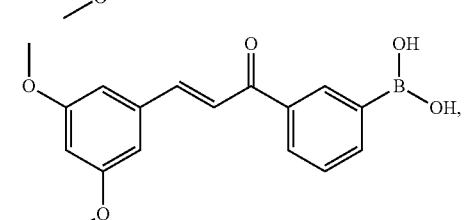
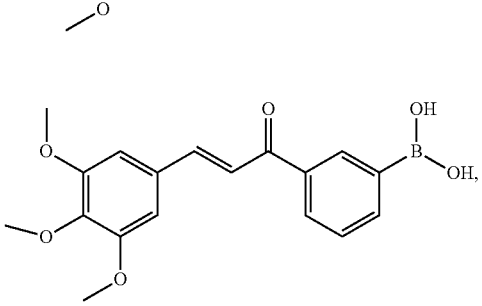

43
-continued
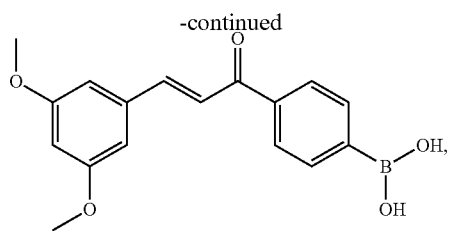
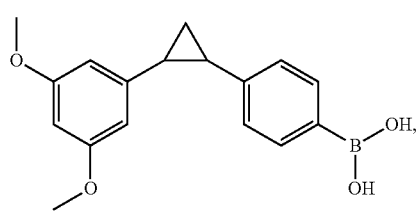
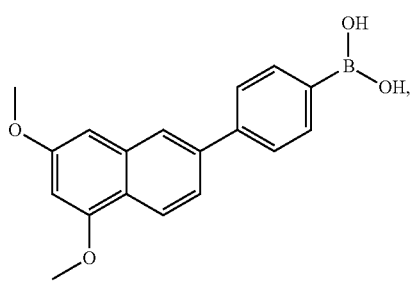
44
-continued
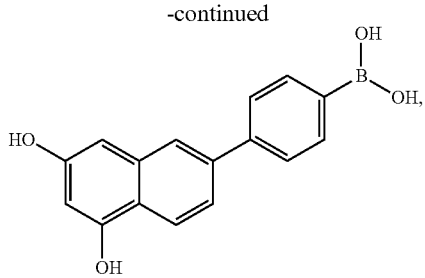
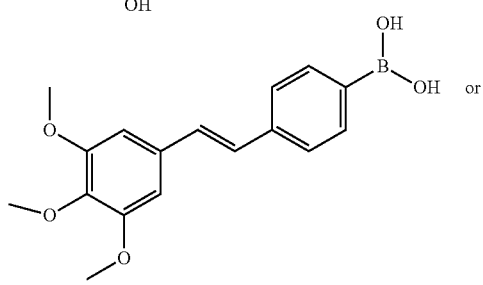 or
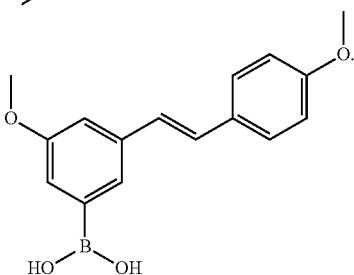
* * * * *

UNITED STATES PATENT AND TRADEMARK OFFICE
CERTIFICATE OF CORRECTION

| | |
|---|---|
| PATENT NO. | : 10,478,445 B2 |
| APPLICATION NO. | : 14/902783 |
| DATED | : November 19, 2019 |
| INVENTOR(S) | : Insoo Bae et al. |

It is certified that error appears in the above-identified patent and that said Letters Patent is hereby corrected as shown below:

In the Specification

Column 1, Lines 16-19, replace the following paragraph:
"This invention was made with government support under 1R03CA152530 awarded by the National Institutes of Health (NIH). The government has certain rights in the invention."

With the following paragraph:
--This invention was made with government support under CA152530 awarded by the National Institutes of Health. The government has certain rights in the invention.--

Signed and Sealed this
Fourteenth Day of November, 2023

Katherine Kelly Vidal
*Director of the United States Patent and Trademark Office*